United States Patent
Tam et al.

(10) Patent No.: US 8,138,221 B2
(45) Date of Patent: Mar. 20, 2012

(54) PHARMACEUTICALLY ACCEPTABLE SALTS OF THYMODEPRESSIN AND PROCESSES FOR THEIR MANUFACTURE

(76) Inventors: Tim Fat Tam, Vaughan (CA); Blaise N'Zemba, Brampton (CA); Regis Leung-Toung, Mississuaga (CA); Yingsheng Wang, Toronto (CA); Yanqing Zhao, Toronto (CA); Lily Yu, Woodbridge (CA)

( * ) Notice: Subject to any disclaimer, the term of this patent is extended or adjusted under 35 U.S.C. 154(b) by 15 days.

(21) Appl. No.: 12/520,337

(22) PCT Filed: Dec. 13, 2007

(86) PCT No.: PCT/CA2007/002235
§ 371 (c)(1),
(2), (4) Date: Jun. 19, 2009

(87) PCT Pub. No.: WO2008/074128
PCT Pub. Date: Jun. 26, 2008

(65) Prior Publication Data
US 2010/0056803 A1    Mar. 4, 2010

(30) Foreign Application Priority Data
Dec. 19, 2006 (CA) ..................... 2571645

(51) Int. Cl.
*A61K 31/404* (2006.01)
*C07D 209/12* (2006.01)
(52) U.S. Cl. ...................... 514/419; 548/495
(58) Field of Classification Search .............. 548/495
See application file for complete search history.

(56) References Cited

U.S. PATENT DOCUMENTS

| 5,736,519 | A | 4/1998 | Deigin et al. |
| 5,902,790 | A | 5/1999 | Green et al. |
| 6,162,442 | A | 12/2000 | Lotter et al. |
| 6,410,515 | B1 | 6/2002 | Deigin et al. |

FOREIGN PATENT DOCUMENTS

| DE | 3400603 A1 | 7/1985 |
| EP | 108937 A2 | 5/1984 |
| WO | WO9854351 A1 | 12/1998 |
| WO | WO9933799 A1 | 7/1999 |

OTHER PUBLICATIONS

Bastin, et al. Organic Process Research & Development 2000, 4, 427-435.*
Haleblian, et al. Journal of Pharmaceutical Sciences 1969, 58, 911-925.*
RN 863988-88-9 retrieved from Registry entered in STN on Sep. 27, 2005.*
Sapuntsova, S.G., et al. (May 2002), Bulletin of Experimental Biology and Medicine, 133(5), 488-490.
Kashirin, D.M. et al. (2000), Pharmaceutical Chemistry Journal, 34(11), 619-622.
Semina, O.V. et al., Effects of iEW Synthetic Peptide Isomers on Bone Marrow Colony-Forming . . . ; Bulletin of Experimental Biology and Medicine, 2005, vol. 140, pp. 348-351.
Korotky, N.G. et al.; Clinical Potential of Thymodepressin in Patient With Psoriasis . . . , Vestnik Dermatologii i Veneralogii, 2002, No. 4, pp. 58-60.
Iyo, Hiromi et al., Sequence-dependent Interaction of Acidic Amino Acid with . . . , Chemical & Pharmaceutical Bulletin, 1991, vol. 39, pp. 2483-2486.
Schmidbaur, Hubert et al., Potassium Hydrogen L-glutamate Monohydrate K (L-GluH), H2O, Chemische Berichte, 1990, vol. 123, pp. 1001-1004.
Wiesbrock, Frank t al, Lithium L-hydrogen Alpha Glutamate . . . Cryst. Eng. Comm, 2003, vol. 5, pp. 262-264.
Kramell, R. et al, Synthesis of N-(jasmonoyl) Amino Conjugates, Tetrahedron, 1988, vol. 44, pp. 5791-5807.

* cited by examiner

*Primary Examiner* — Shawquia Young

(57) ABSTRACT

The present invention relates to pharmaceutically acceptable crystalline and amorphous salts of D-isoglutamyl-D-tryptophan as well as processes for their manufacture, pharmaceutical compositions comprising them, and their uses in the preparation of pharmaceutical compositions for the treatment of various conditions and/or diseases. In particular, the present invention relates to D-isoglutamyl-D-tryptophan potassium salt (1:1), D-isoglutamyl-D-tryptophan lithium salt (1:1), D-isoglutamyl-D-tryptophan calcium salt (2:1), D-isoglutamyl-D-tryptophan magnesium salt (2:1), and D-isoglutamyl-D-tryptophan organic ammonium salts (1:1).

8 Claims, 15 Drawing Sheets

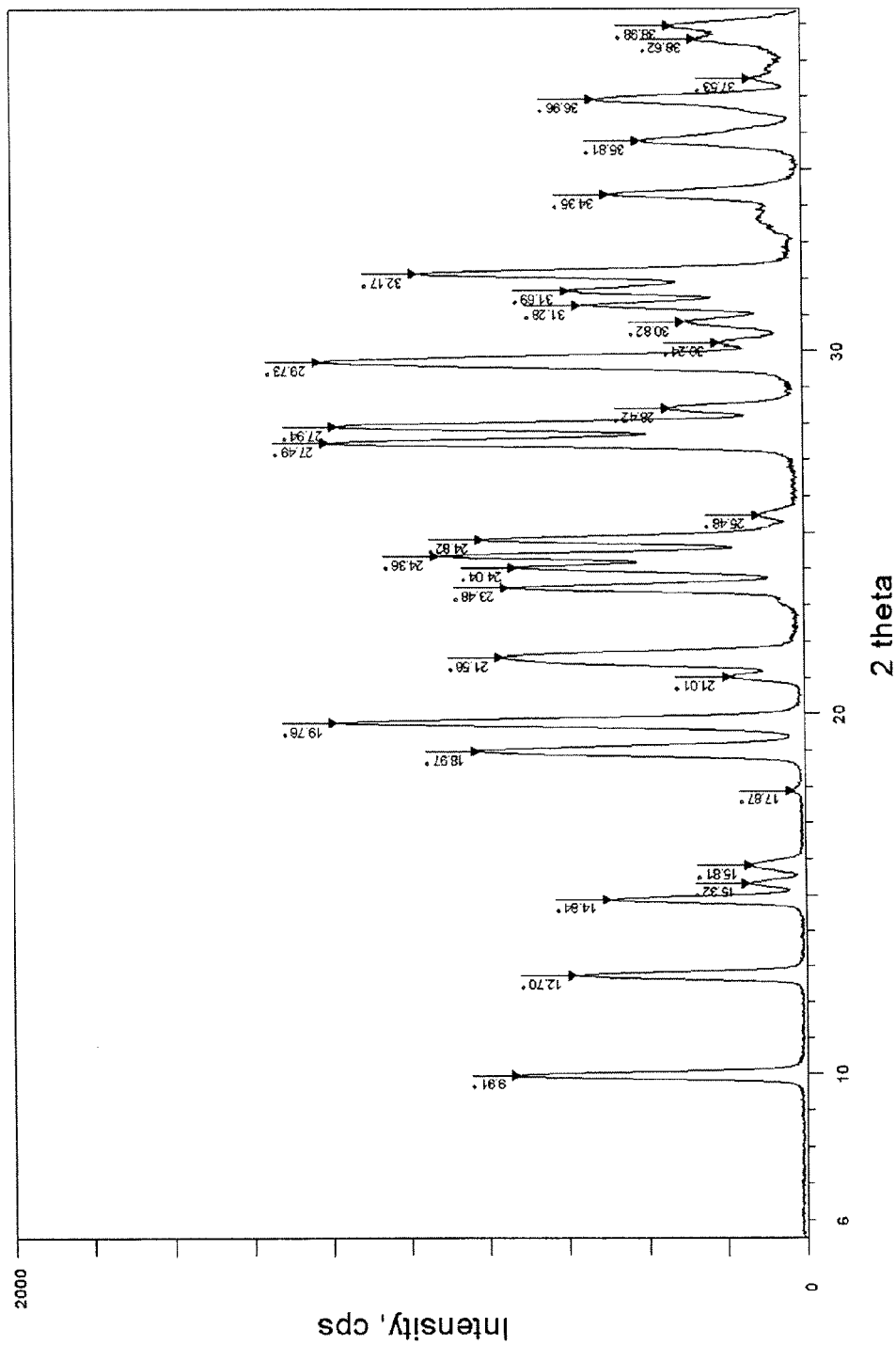
Fig. 1A: Powder X-ray Diffraction Pattern of potassium salt of D-isoglutamyl-D-tryptophan (1 : 1)

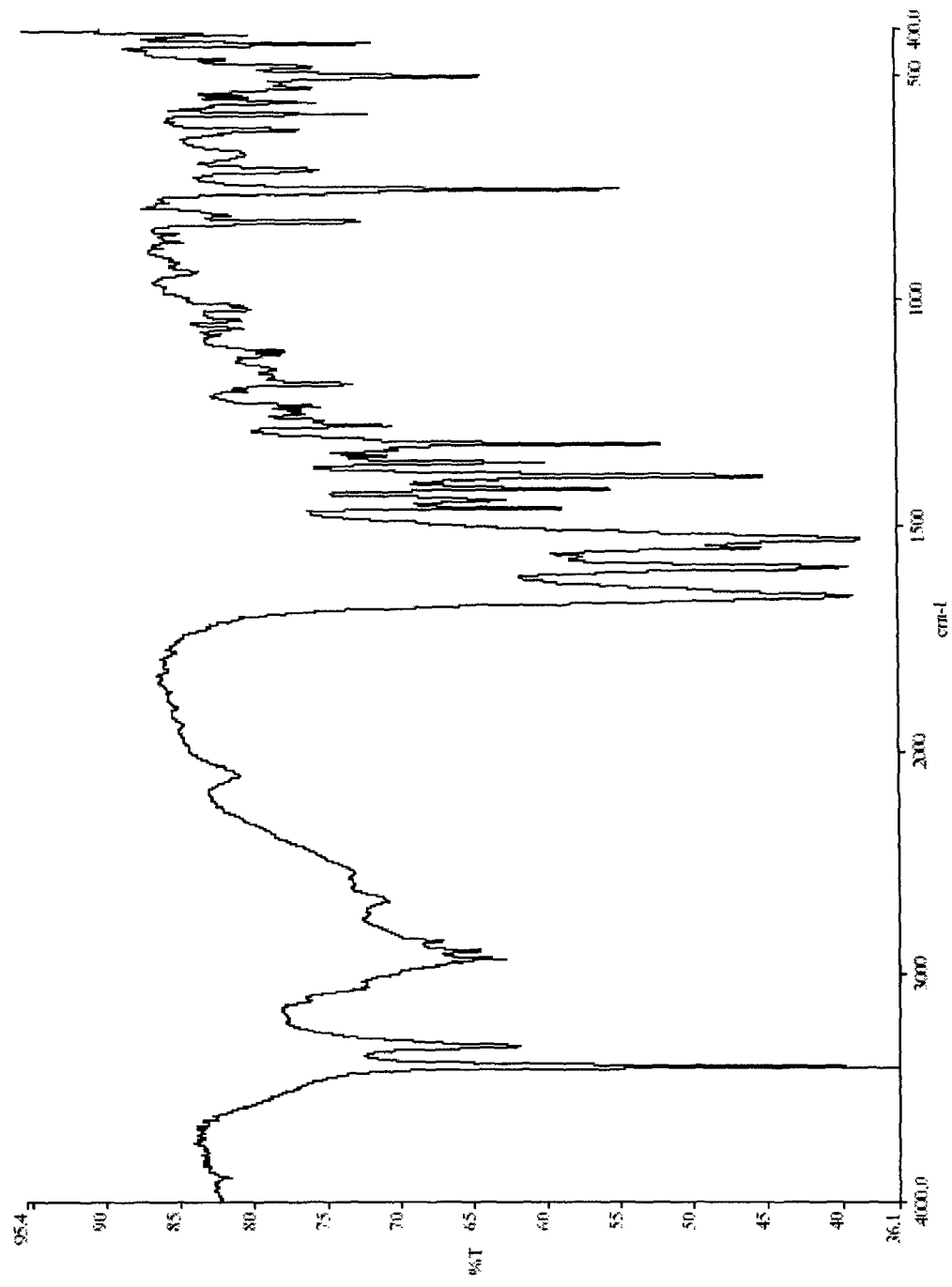
Fig. 1B: FTIR spectrum of crystalline potassium salt of D-isoglutamyl-D-tryptophan (1 : 1)

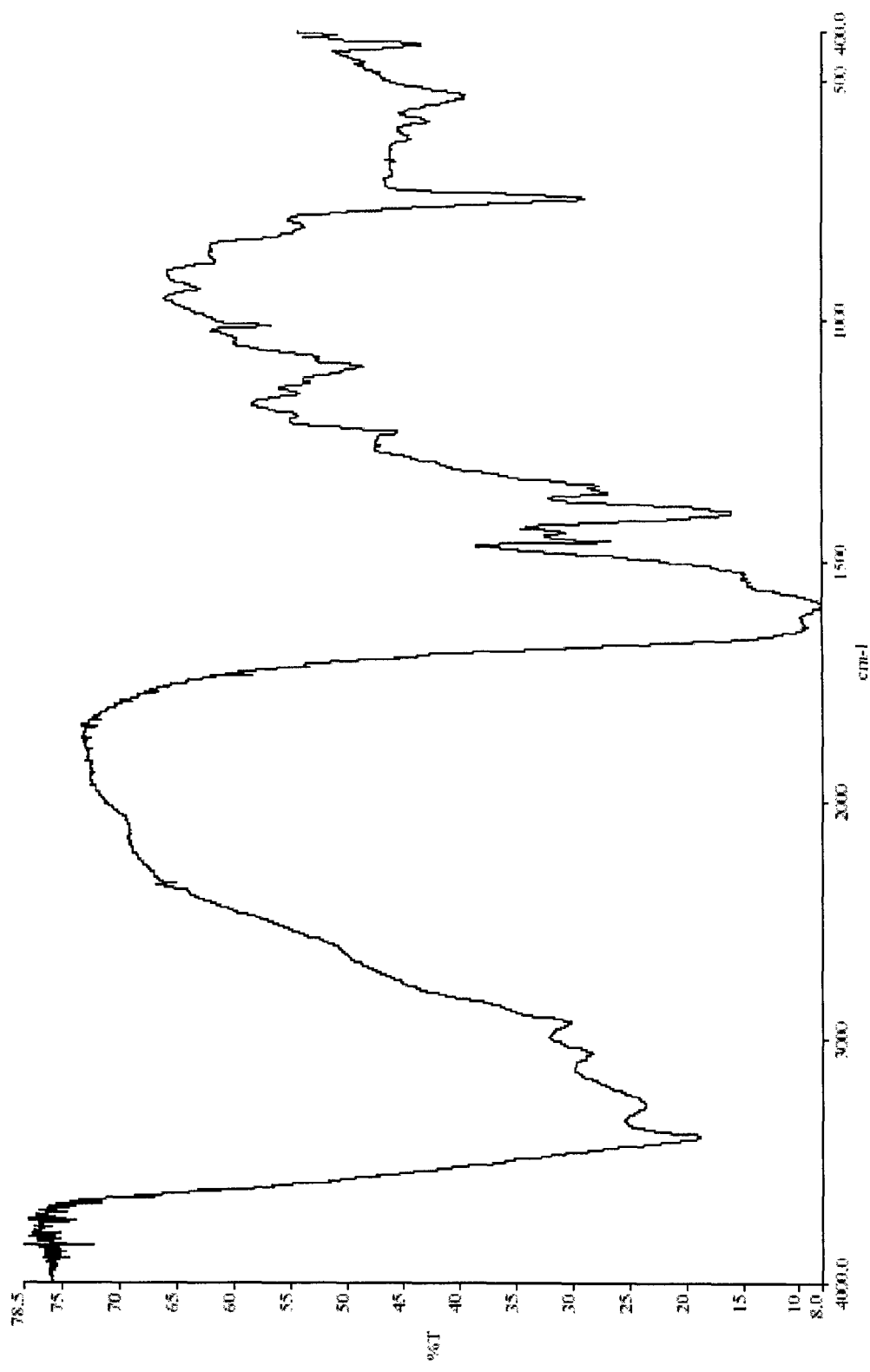
Fig. 1C: FTIR Spectrum of Amorphous Potassium Salt of D-isoglutamyl-D-tryptophan (1 : 1)

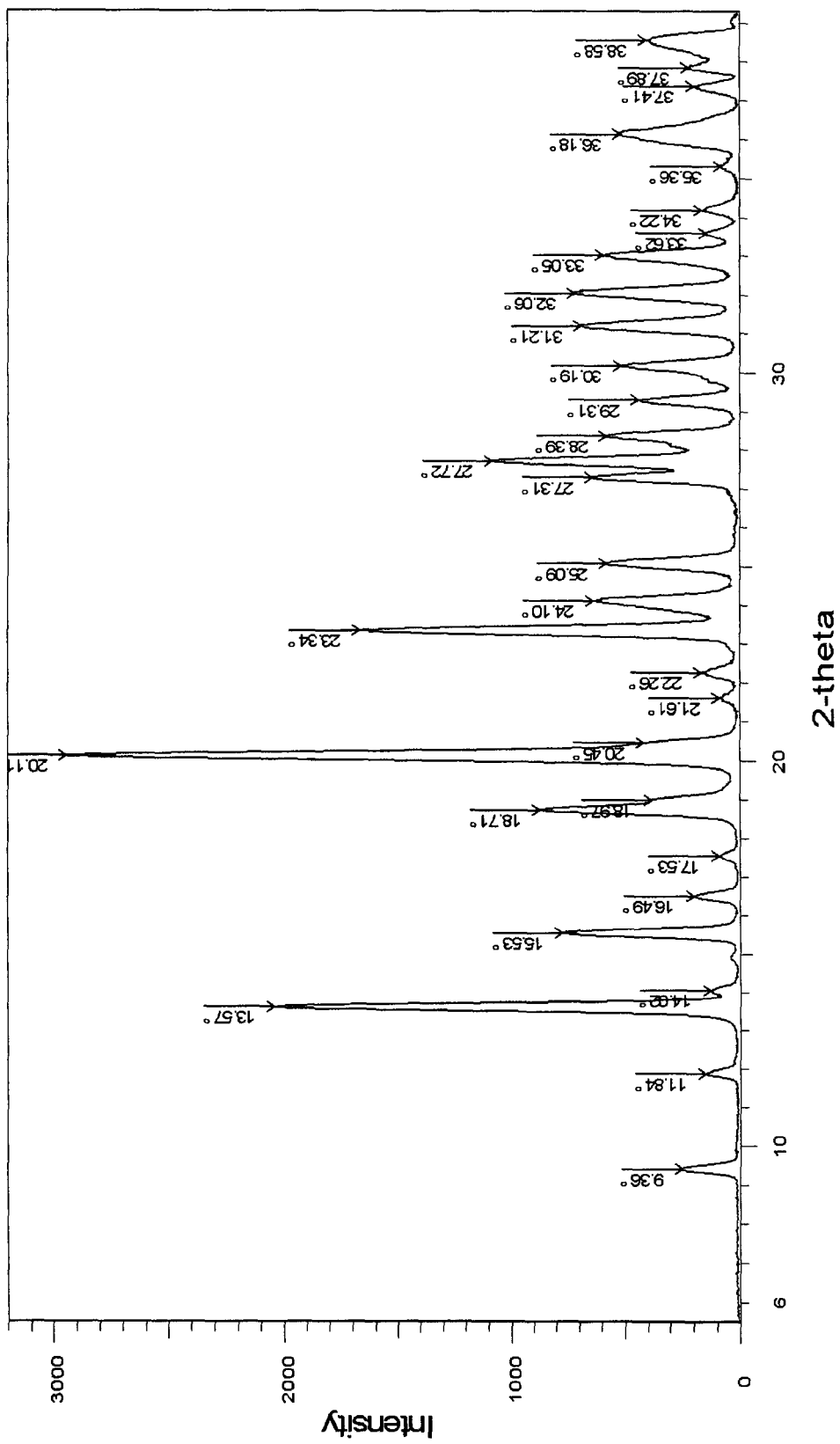
Fig. 2A: Powder X-ray Diffraction Pattern of Lithium Salt of D-isoglutamyl-D-tryptophan (1 : 1)

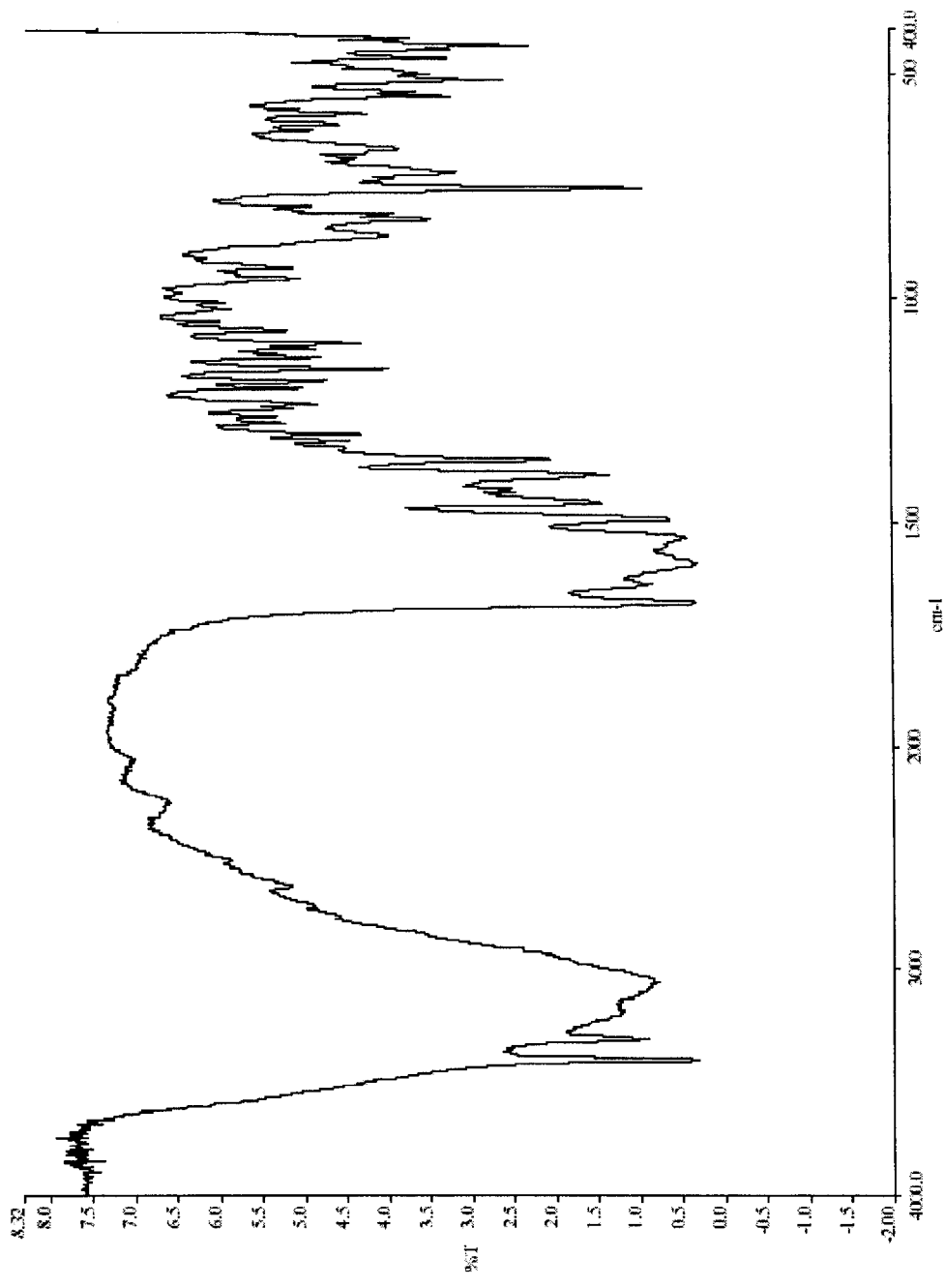
Fig. 2B: FTIR spectrum of crystalline mono lithium salt of D-isoglutamyl-D-tryptophan (1 : 1)

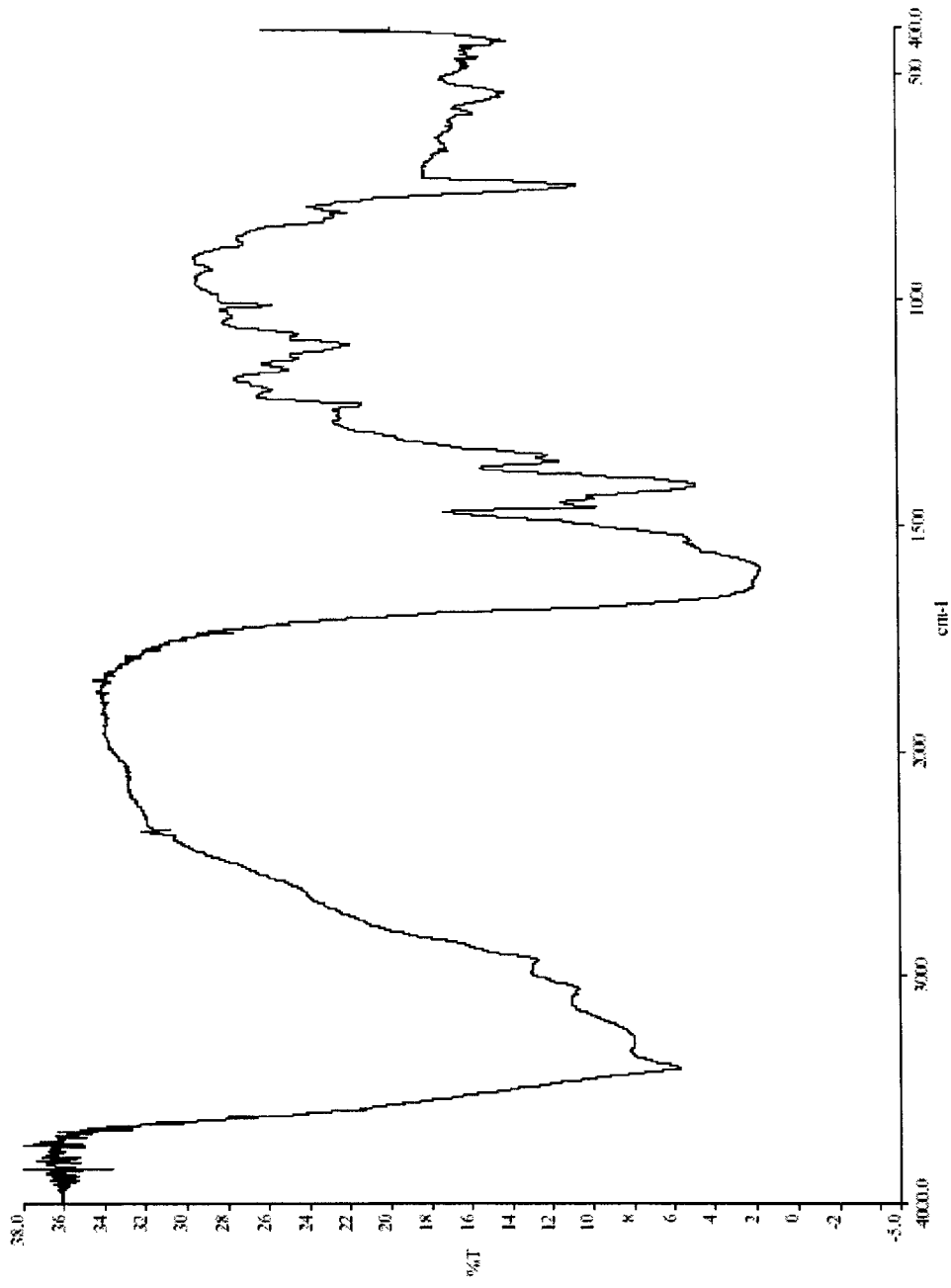

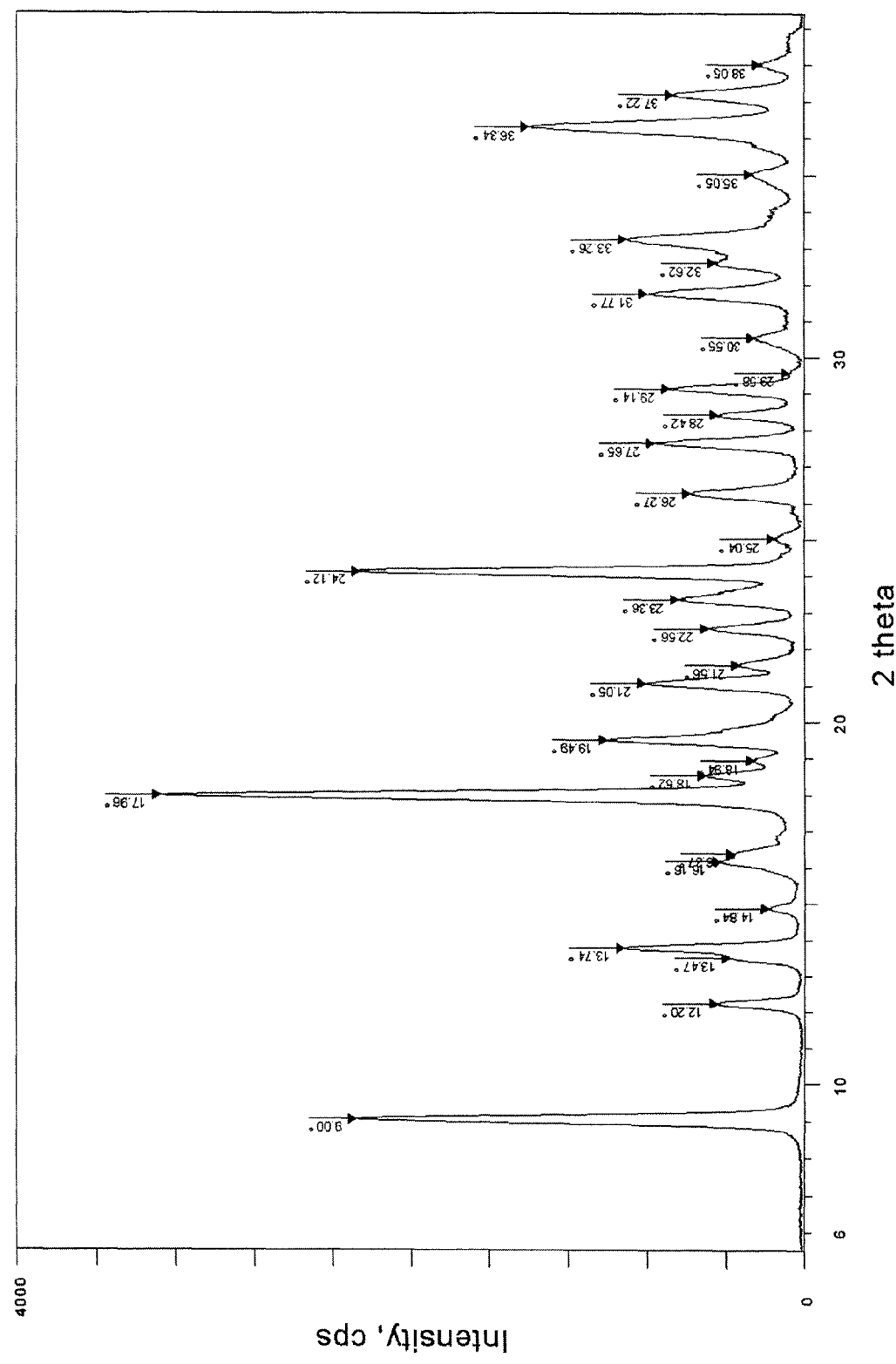
Fig. 3A: Powder X-ray Diffraction Pattern of Magnesium salt of D-isoglutamyl-D-tryptophan (1 : 2)

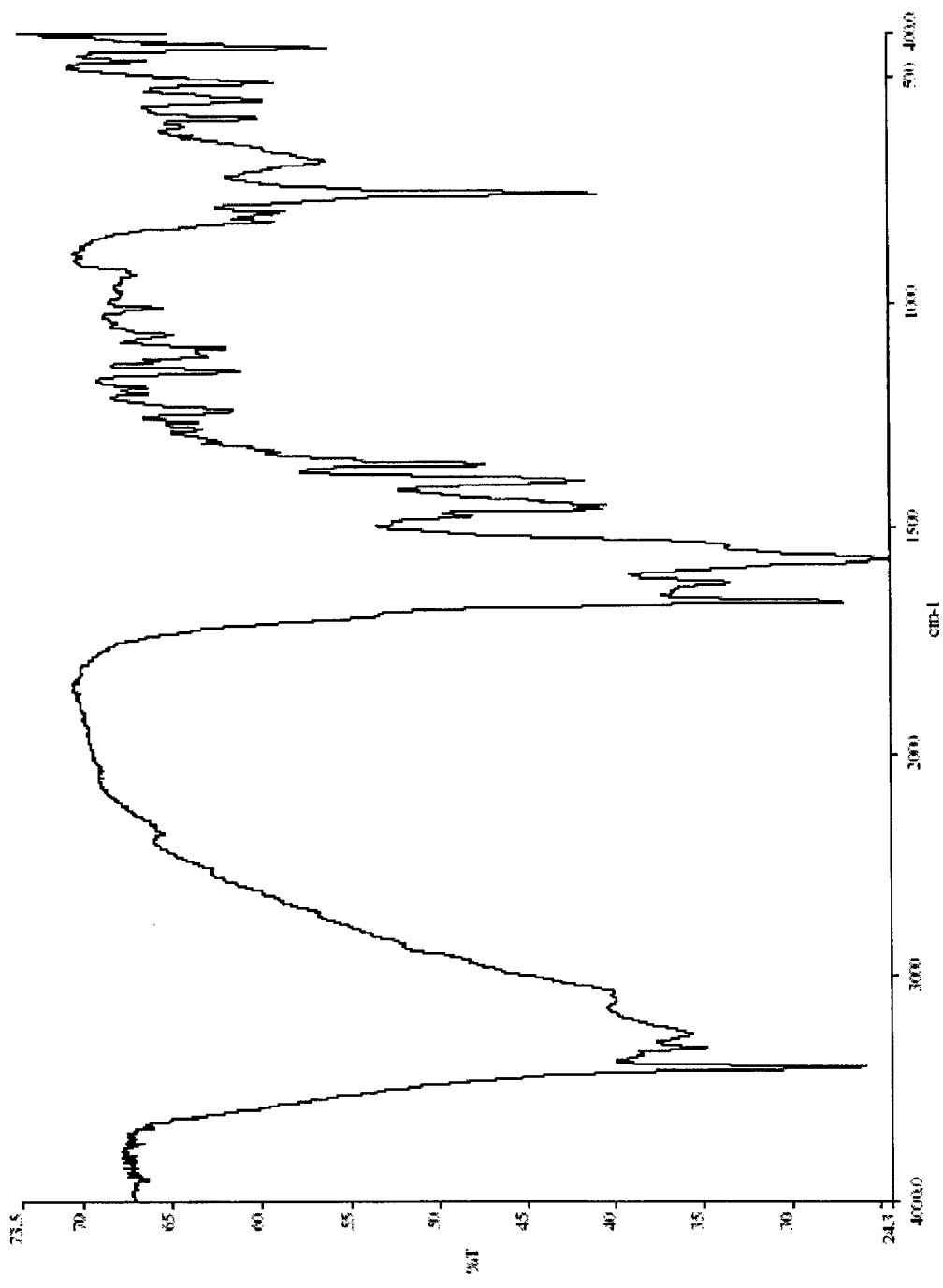
Fig. 3B: FTIR spectrum of Magnesium salt of D-isoglutamyl-D-tryptophan (1 : 2)

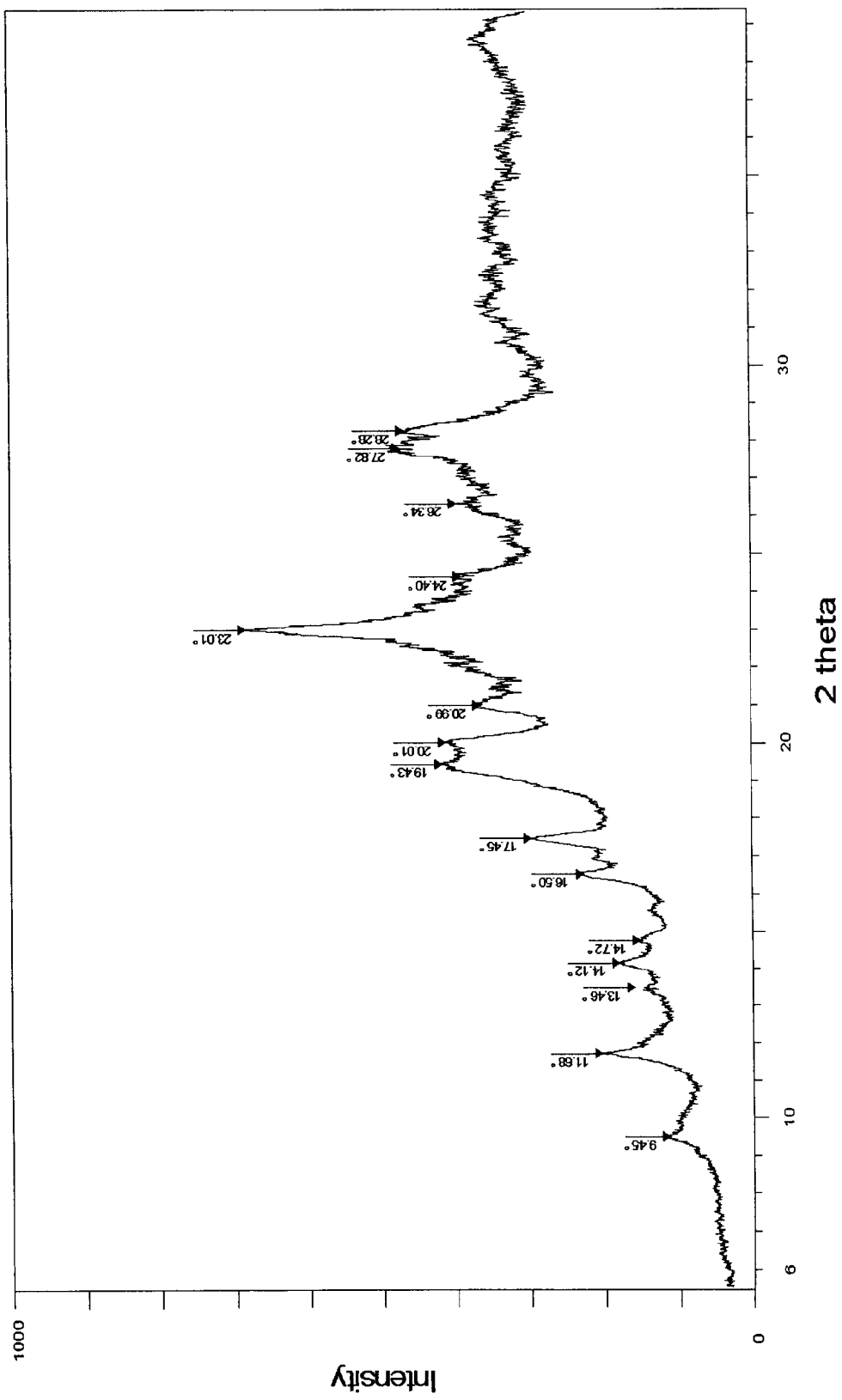
Figure 4A: Powder X-ray Diffraction Pattern of Calcium salt of D-isoglutamyl-D-tryptophan (1 : 2)

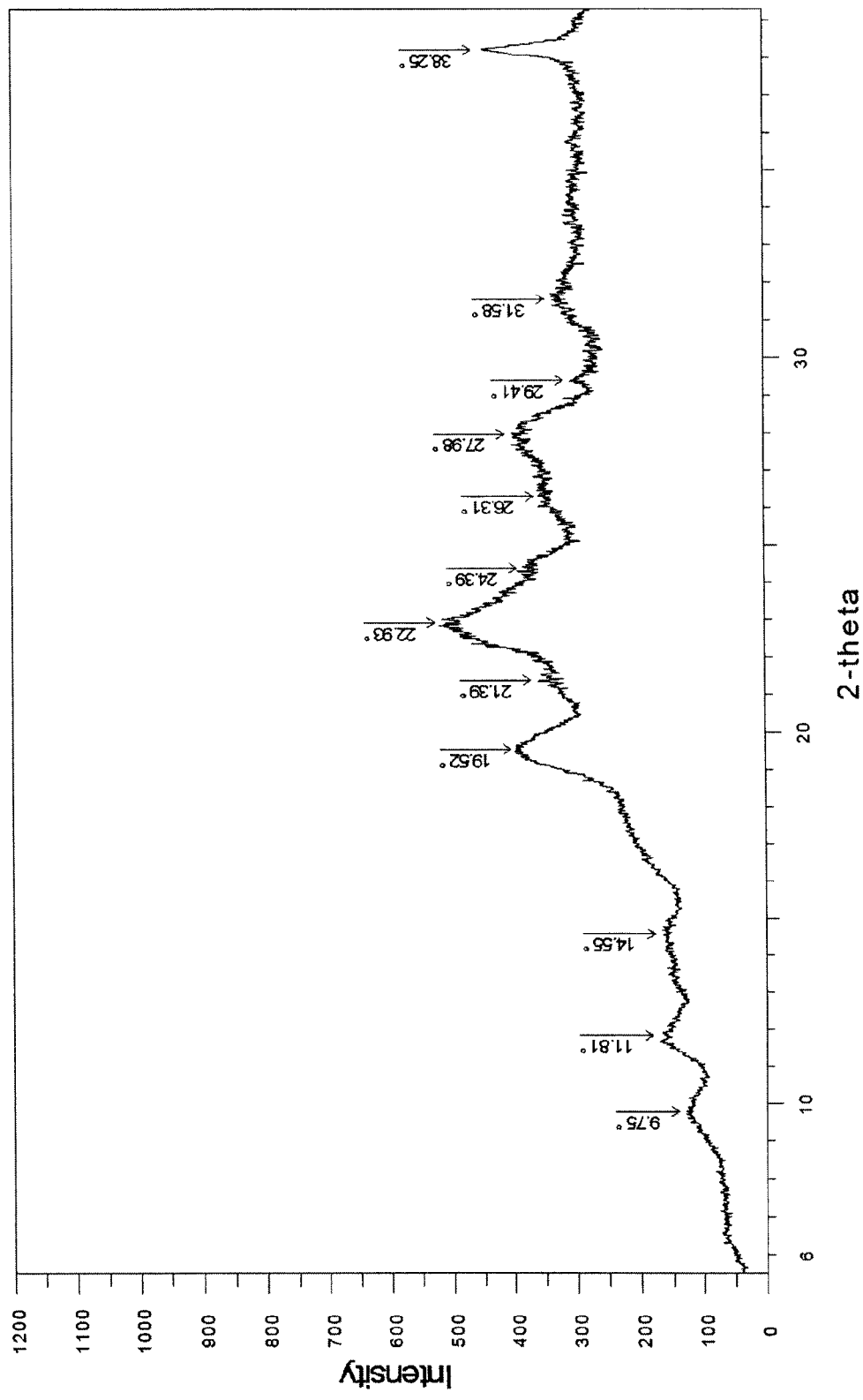
Fig. 4B: Powder X-ray Diffraction Pattern of Calcium Salt of D-isoglutamyl-D-tryptophan (1 : 2)

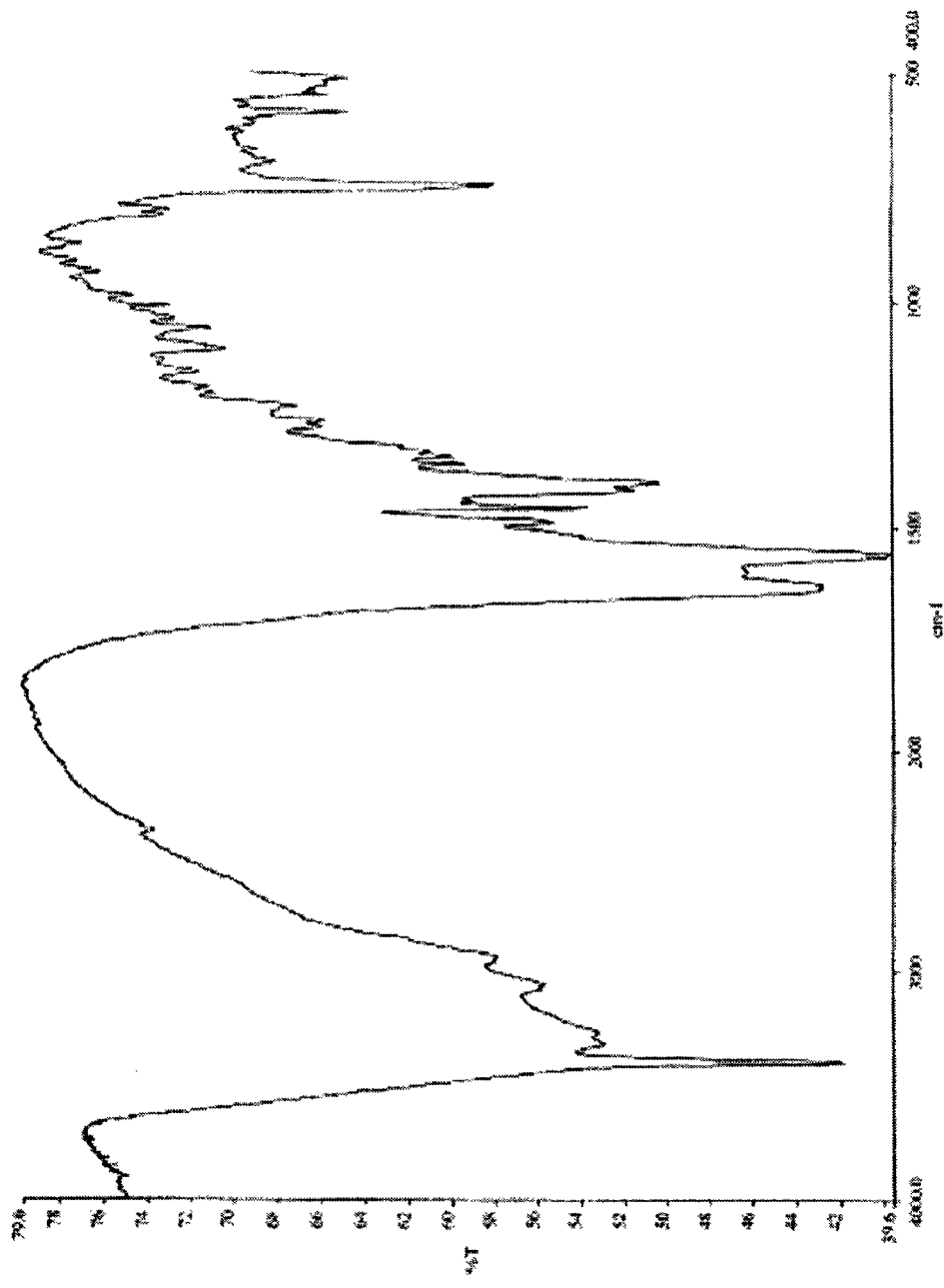
Fig. 4C: FTIR spectrum of calcium salt of D-isoglutamyl-D-tryptophan (1 : 2)

Fig. 5: Speciation plot of H-D-iGlu-D-Trp-OH from pH 0 to 12
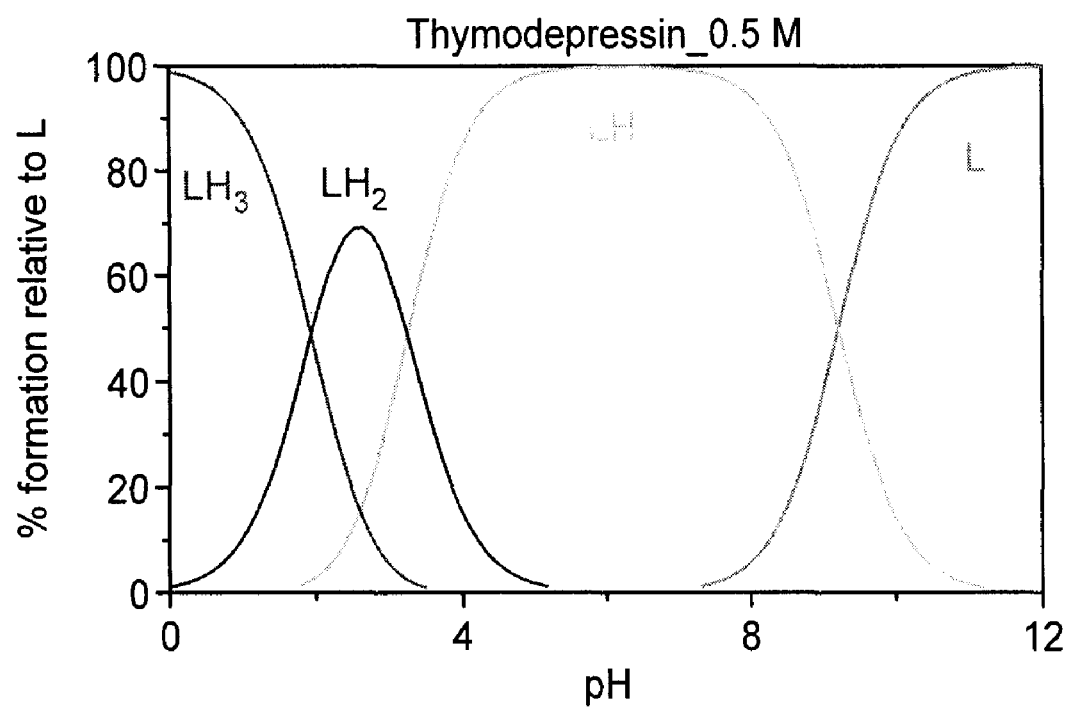

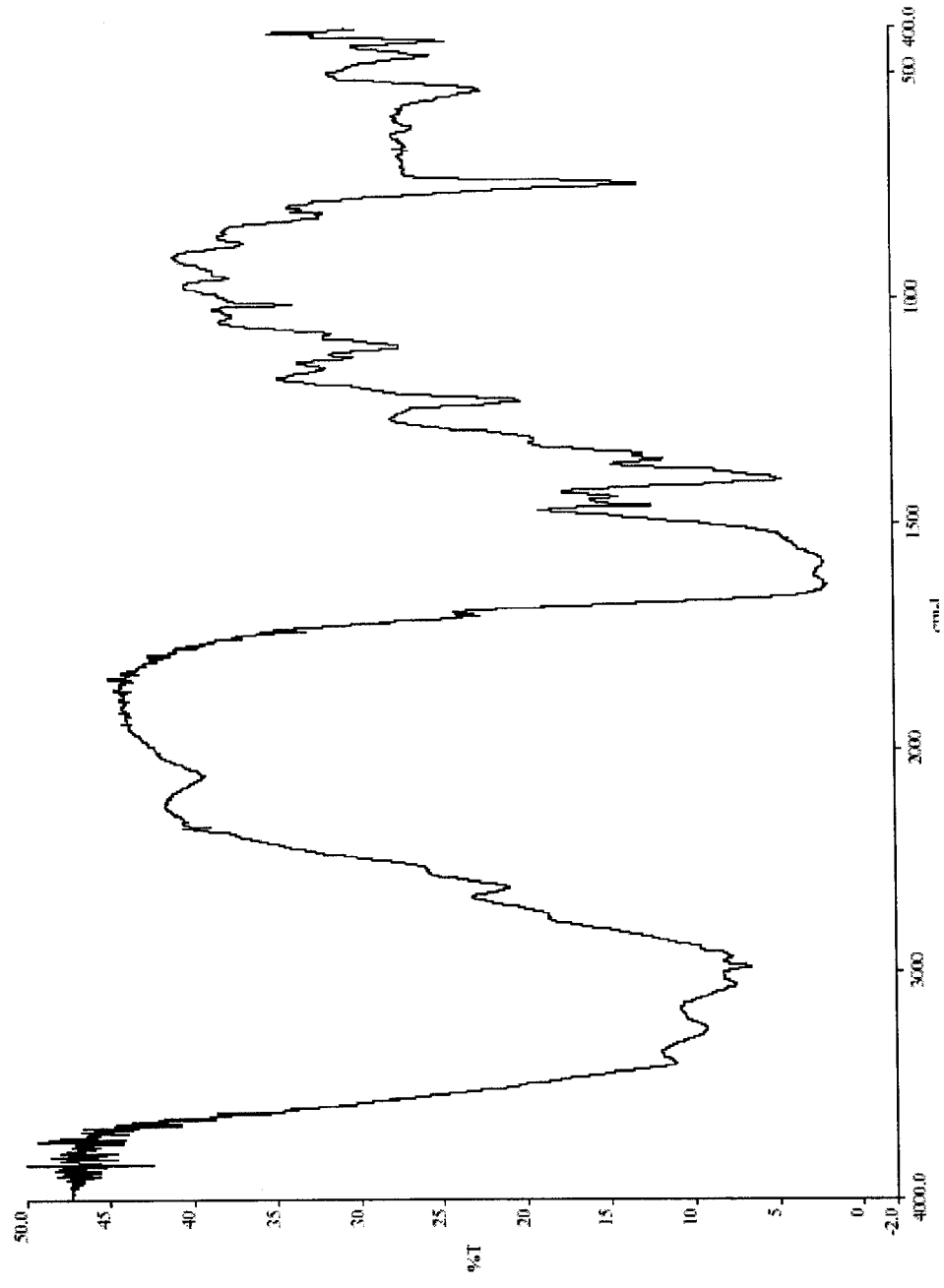
Fig. 6: FTIR (KBr) spectrum of amorphous salt of tert-butylamine and D-isoglutamyl-D-tryptophan (1 : 1)

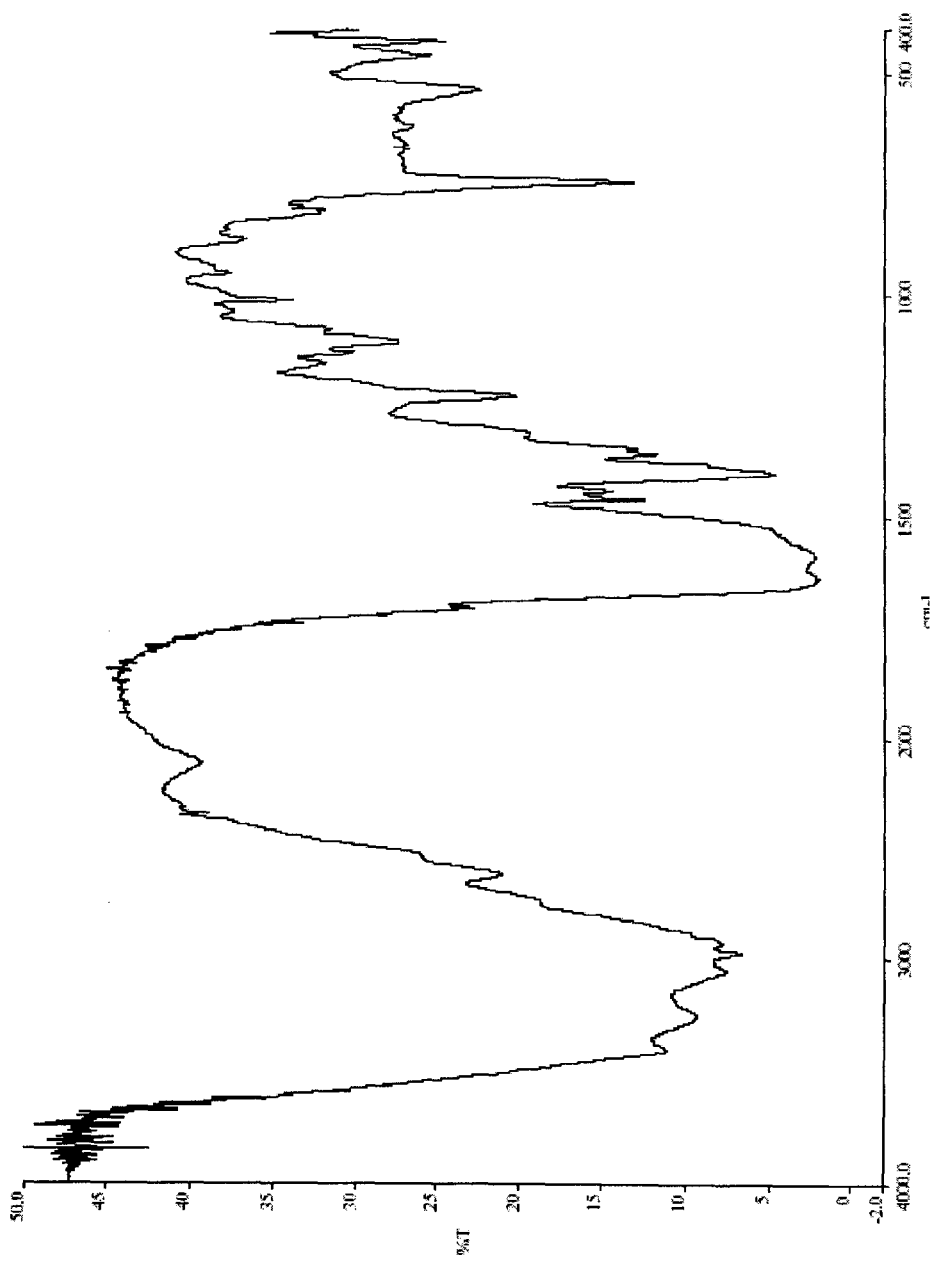
Fig. 7: FTIR (KBr) spectrum of amorphous mono tris(hydroxymethyl)aminomethane salt of D-isoglutamyl-D-tryptophan (1 : 1)

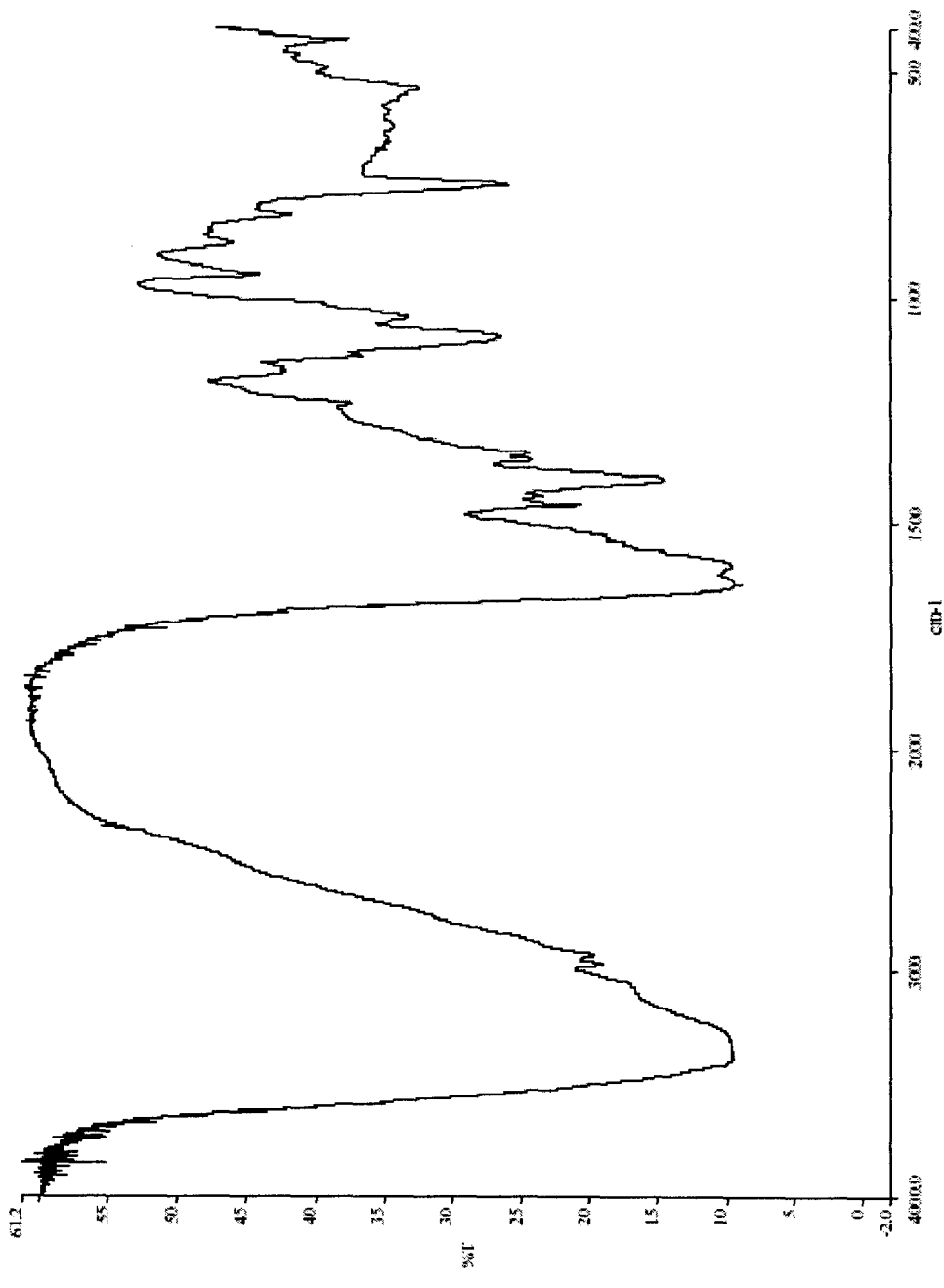
Fig. 8: FTIR (KBr) spectrum of amorphous mono N-methyl-D-glucamine salt of D-isoglutamyl-D-tryptophan (1 : 1)

PHARMACEUTICALLY ACCEPTABLE SALTS OF THYMODEPRESSIN AND PROCESSES FOR THEIR MANUFACTURE

FIELD OF THE INVENTION

The present invention relates to novel crystalline and amorphous pharmaceutically acceptable salts of D-isoglutamyl-D-tryptophan. In particular, the present invention relates to D-isoglutamyl-D-tryptophan potassium salt (1:1), D-isoglutamyl-D-tryptophan lithium salt (1:1), D-isoglutamyl-D-tryptophan calcium salt (2:1), D-isoglutamyl-D-tryptophan magnesium salt (2:1), and D-isoglutamyl-D-tryptophan organic ammonium salts (1:1) which have improved properties over amorphous D-isoglutamyl-D-tryptophan, crystalline D-isoglutamyl-D-tryptophan and D-isoglutamyl-D-tryptophan disodium salt. The present invention also relates to processes for the manufacture of these novel salts of D-isoglutamyl-D-tryptophan.

BACKGROUND OF THE INVENTION

The compound D-isoglutamyl-D-tryptophan (also known as H-D-iGlu-D-Trp-OH or Thymodepressin) is a synthetic hemoregulatory dipeptide having the following formula:

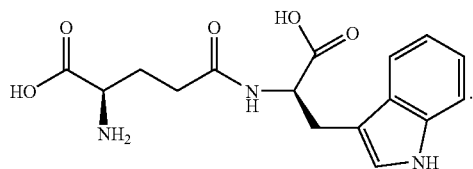

Thymodepressin is the free diacid having Chemical Abstracts Service (CAS) Registry Number® of 186087-26-3. U.S. Pat. No. 5,736,519 discloses H-D-iGlu-D-Trp-OH and a process for its preparation wherein it is purified by ion exchange chromatography. It is an immunosuppressant and selectively inhibits proliferation of hemopoietic precursor cells and stimulates granulocyte and lymphocyte apoptosis (Sapuntsova, S. G., et al. (May 2002), Bulletin of Experimental Biology and Medicine, 133(5), 488-490).

Thymodepressin is currently being sold in Russia as the disodium salt of D-isoglutamyl-D-tryptophan in liquid formulation for injection and intranasal administration for the treatment of psoriasis and atopic dermatitis. The solid form of the disodium salt of D-isoglutamyl-D-tryptophan is an amorphous powder which is hygroscopic and very difficult to handle. The disodium salt of D-isoglutamyl-D-tryptophan has the molecular formula $C_{16}H_{17}N_3Na_2O_5$ and the following chemical structure:

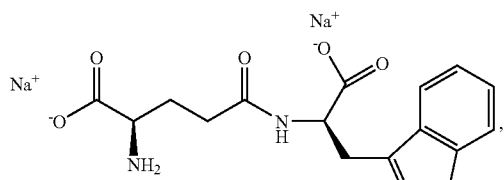

which is reported in Kashirin, D. M., et al. (2000), Pharmaceutical Chemistry Journal, 34(11), 619-622.

Through investigations in our laboratory, we have determined that the freeze-dried disodium salt of D-isoglutamyl-D-tryptophan is extremely hygroscopic turning into a gel in a matter of minutes in air and cannot easily be handled.

A powdery or amorphous form of a compound, intended for pharmaceutical use may give rise to manufacturing problems due to bulk density issues, hygroscopicity and variable water content that cannot be corrected by vacuum drying. D-isoglutamyl-D-tryptophan is a dipeptide and the drying of an amorphous form at elevated temperature, for example, 80-100° C. under vacuum is not recommended. Thus, there are serious difficulties experienced during the purification of the disodium salt of D-isoglutamyl-D-tryptophan and obtaining the pure disodium salt on a manufacturing scale. Further, there is no published procedure for its preparation.

The monosodium salt of D-isoglutamyl-D-tryptophan is identified by the CAS Registry Registry System and is listed in the CAS REGISTRY$^{SM}$ File with a CAS Registry Number® of 863988-88-9. However, there are no references citing the substance and thus no publication of its identity, its physical and/or chemical properties, its characterization or a procedure for its preparation. Freeze-dried powders of mono sodium and disodium salts of peptide drugs may not have controllable powder bulk density ranges for formulation. They may require significant investment in freeze-dried dispersion technology.

Therefore, there is a need to develop alternative pharmaceutically acceptable salts of D-isoglutamyl-D-tryptophan which are crystalline. Such crystalline salts can generally be purified more easily than an amorphous form and may possess other advantageous properties, for example in relation to their particular crystalline form and/or their solubility characteristics and/or their lack of hygroscopicity and/or their stability characteristics, including their thermal stability properties and/or their ability to undergo oxidative degradation.

SUMMARY OF THE INVENTION

An object of the present invention is to provide a number of novel, stable and pharmaceutically acceptable salts of thymodepressin for formulation development.

Not all salts of D-isoglutamyl-D-tryptophan are chemically stable (such as, for example, the amorphous disodium salt). However, we have invented stable, novel metal, and organic ammonium salts of D-isoglutamyl-D-tryptophan (H-D-i-Glu-D-Trp-OH), which provide the basis for the present invention.

In one aspect of the present invention, there is provided novel salts of D-isoglutamyl-D-tryptophan. These novel salt forms are compounds of formula I,

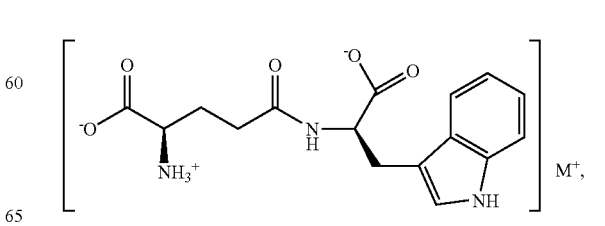

wherein M is selected from the group consisting of lithium and potassium; formula II,

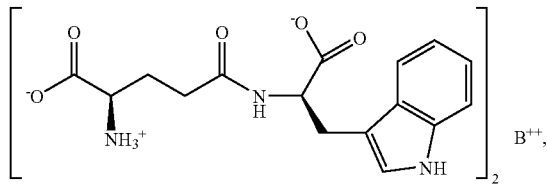

wherein B is selected from the group consisting of magnesium and calcium; and formula III,

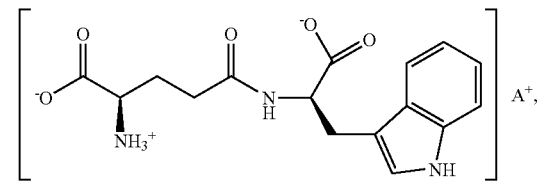

wherein A is selected from the group consisting of tert-butylammonium, tris(hydroxymethyl)methylammonium and methyl-(2,3,4,5,6-pentahydroxy-hexyl)-ammonium.

Particularly, in the novel salts of formula I, the lithium or potassium cation displaces one hydrogen atom, on the carboxylic portion of the compound D-isoglutamyl-D-tryptophan. It has been determined in our laboratory that the novel salts of formula I of the present invention, wherein M is potassium (i.e. the mono potassium salt of D-isoglutamyl-D-tryptophan), can exist in different forms, in particular in amorphous or non-crystalline form and in crystalline form. It has also been determined in our laboratory that the novel salts of formula I of the present invention, wherein M is lithium (i.e. the mono lithium salt of D-isoglutamyl-D-tryptophan), can exist in different forms, in particular in amorphous or non-crystalline form and in crystalline form. Therefore, the present invention relates to the mono lithium and mono potassium salts of D-isoglutamyl-D-tryptophan in any of their forms.

In another aspect of the present invention, there is provided novel lithium, and potassium salts of D-isoglutamyl-D-tryptophan, the compound of formula I.

In another aspect of the present invention, there is provided the crystalline potassium salt of D-isoglutamyl-D-tryptophan, the compound of formula I.

In another aspect of the present invention, there is provided the crystalline lithium salt of D-isoglutamyl-D-tryptophan, the compound of formula I.

The present invention also relates to a crystalline form of the magnesium salt of D-isoglutamyl-D-tryptophan and a semi-crystalline of the calcium salt of D-isoglutamyl-D-tryptophan wherein the calcium or magnesium cation displaces one hydrogen atom on the carboxylic portion of the compound of D-isoglutamyl-D-tryptophan. The D-isoglutamyl-D-tryptophan calcium or magnesium salt is formed in the ratio 2:1 as illustrated in formula II.

It has been determined in our laboratory that the magnesium salt of the present invention (i.e. the magnesium salt of thymodepressin [1:2]) exists in crystalline form, while the calcium salt of the present invention (i.e. the calcium salt of thymodepressin [1:2]) is semi-crystalline with the percent crystallinity not exceeding about 67%.

In another aspect of the present invention, there is provided the novel crystalline magnesium salt of D-isoglutamyl-D-tryptophan, the compound of formula II.

In another aspect of the present invention, there is provided the calcium salt of D-isoglutamyl-D-tryptophan, the compound of formula II.

The present invention also relates to the organic amine salts of formula III wherein A is selected from the group consisting of tert-butylammonium, tris(hydroxymethyl)methylammonium, and methyl-(2,3,4,5,6-pentahydroxy-hexyl)-ammonium. It has been determined in our laboratory that these salts of formula III are amorphous.

In another aspect of the present invention, there is provided the novel tert-butylammonium, tris(hydroxymethyl)methylammonium, methyl-(2,3,4,5,6-pentahydroxy-hexyl)-ammonium salt of D-isoglutamyl-D-tryptophan, the compound of formula III.

In another aspect of the present invention, there is provided a process for preparing the salts of formulas I, II, and III from the dipeptide D-isoglutamyl-D-tryptophan.

In another aspect of the present invention, there is provided a process for preparing said salts of D-isoglutamyl-D-tryptophan (the compound of formula I, and II) from salt exchange of the D-isoglutamyl-D-tryptophan ammonium salt (1:1).

In an earlier patent application filed in Canada on Nov. 28, 2006, the Applicant discloses methods for the manufacturing of D-isoglutamyl-D-tryptophan and its mono ammonium salt, a novel stable crystalline form of D-isoglutamyl-D-tryptophan and its mono ammonium salt. The D-isoglutamyl-D-tryptophan and its mono ammonium salt used in the present invention may be prepared by the process described in the aforementioned patent application.

In another aspect of the present invention, there is provided a pharmaceutical composition comprising any of the novel salts described above and at least one pharmaceutically acceptable carrier.

The pharmaceutical composition may be prepared by combining any of the novel salts described above and at least one pharmaceutically acceptable carrier. In another aspect of the present invention, there is provided a process for making a pharmaceutical composition comprising combining any of the novel salts described above and at least one pharmaceutically acceptable carrier.

In another aspect of the present invention, there is provided the use of any of the novel salts described herein in the preparation of a medicament for treating psoriasis, in a subject in need thereof.

A further feature of the crystalline salts of the present invention is that they can also advantageously be used as intermediates in the manufacture of the non-crystalline salt, to enable isolation of non-crystalline salt with a purity level and uniformity suitable for formulation to meet exacting pharmaceutical requirements and specifications. Examples of those salts are lithium, sodium, potassium and ammonium salt. Recrystallization techniques generally remove impurities in its process, while the purification of amorphous peptide drug substances requires preparative reverse phase high pressure liquid chromatography, which is not economical.

Other and further advantages and features of the present invention will be apparent to those skilled in the art from the following detailed description thereof taken in conjunction with the accompanying drawings.

BRIEF DESCRIPTION OF THE DRAWINGS

In the accompanying drawings:

FIG. 1A is an X-ray Powder Diffraction (XRPD) pattern of potassium salt of D-isoglutamyl-D-tryptophan (1:1).

FIG. 1B is a Fourier Transform Infrared (FTIR) spectrum of crystalline potassium salt of D-isoglutamyl-D-tryptophan (1:1).

FIG. 1C is an FTIR spectrum of amorphous potassium salt of D-isoglutamyl-D-tryptophan (1:1).

FIG. 2A is an XRPD pattern of Lithium Salt of D-isoglutamyl-D-tryptophan (1:1),

FIG. 2B is an FTIR spectrum of crystalline lithium salt of D-isoglutamyl-D-tryptophan (1:1).

FIG. 2C is an FTIR spectrum of amorphous lithium salt of D-isoglutamyl-D-tryptophan (1:1).

FIG. 3A is an XRPD pattern of Magnesium salt of D-isoglutamyl-D-tryptophan (1:2).

FIG. 3B is an FTIR spectrum of Magnesium salt of D-isoglutamyl-D-tryptophan (1:2).

FIG. 4A is a PXRD pattern of Calcium salt of D-isoglutamyl-D-tryptophan (1:2).

FIG. 4B is a PXRD pattern of Calcium salt of D-isoglutamyl-D-tryptophan (1:2).

FIG. 4C is an FTIR spectrum of calcium salt of D-isoglutamyl-D-tryptophan (1:2) using material from FIG. 4A.

FIG. 5 is a speciation plot of the dipeptide D-isoglutamyl-D-tryptophan at different pHs.

FIG. 6 is an FTIR spectrum of amorphous salt of tert-butylamine and D-isoglutamyl-D-tryptophan (1:1).

FIG. 7 is an FTIR spectrum of amorphous mono tris(hydroxymethyl)aminomethane salt of D-isoglutamyl-D-tryptophan (1:1).

FIG. 8 is an FTIR spectrum of amorphous mono N-methyl-D-glucamine salt of D-isoglutamyl-D-tryptophan (1:1).

DETAILED DESCRIPTION OF THE PREFERRED EMBODIMENTS OF THE INVENTION

As mentioned above, the present invention relates to the novel metal salts and organic amine salts of D-isoglutamyl-D-tryptophan.

As used herein, D-isoglutamyl-D-tryptophan is the free diacid

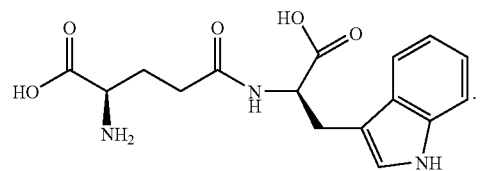

The chemistry of amino acids or simple dipeptides is complicated by the fact that the —$NH_2$ group is a base and the —$CO_2H$ group is an acid. In aqueous solution, an $H^+$ ion is therefore transferred from one end of the molecule to the other to form a zwitterion

Zwitterions are simultaneously electrically charged and electrically neutral. They contain positive and negative charges, but the net charge on the molecule is zero. Although the basis for salt formation is not entirely bound by theory, the iGlu amino acid unit of H-D-iGlu-D-Trp-OH exists as a zwitterion, and therefore, there is only one —$CO_2H$ group left that is available for the formation of a salt when only one equivalent of monovalent metal hydroxide, 0.5 equivalent of divalent metal hydroxide $B(OH)_2$ or one equivalent of organic amine is used to adjust the pH to neutral conditions. Examples of monovalent metal hydroxides are sodium hydroxide, lithium hydroxide and potassium hydroxide. Examples of divalent metal hydroxides are calcium hydroxide and magnesium hydroxide.

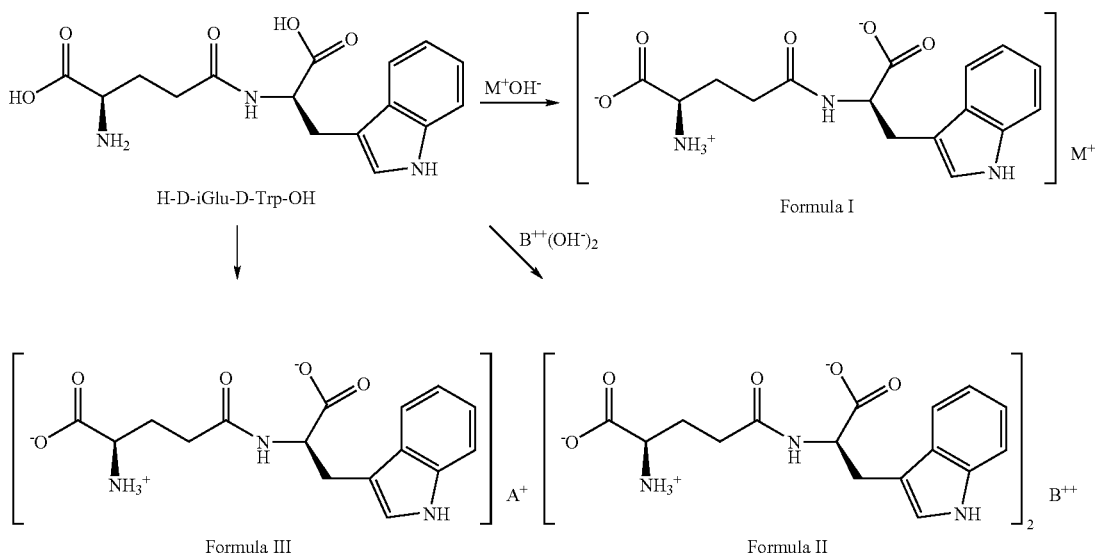

When H-D-iGlu-D-Trp-OH monovalent metal salt of formula I is drawn in the format shown above, only one $CO_2H$ group can accommodate one monovalent metal to give the salt of formula I. Examples of those monovalent salts of the present invention are potassium and lithium salt (1:1). Examples of the divalent metal salts of the present invention are the magnesium and calcium salts. Examples of the organic amine salts of the present invention are the tert-butylammonium, tris(hydroxymethyl)methylammonium, and methyl-(2,3,4,5,6-pentahydroxy-hexyl)-ammonium salts.

Although the prior art literature has loosely used the term thymodepressin to represent both the free diacid of D-isoglutamyl-D-tryptophan and its disodium salt, within the context of the present invention, thymodepressin is the free diacid of D-isoglutamyl-D-tryptophan with the molecular formula $C_{16}H_{19}N_3O_5$ and the disodium salt is the compound with the molecular formula $C_{16}H_{17}N_3Na_2O_5$. They are two different chemical entities having different physical and chemical properties.

As used herein, the mono lithium or potassium salt is formed by the replacement of one carboxylic group hydrogen with the metal ion lithium or potassium with the structure shown in formula I above. The specific structures are shown below:

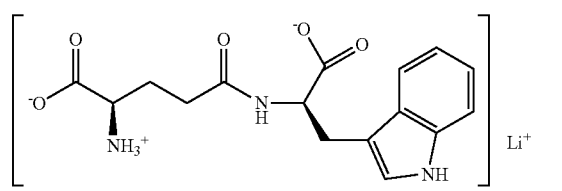

Lithium salt of Formula I

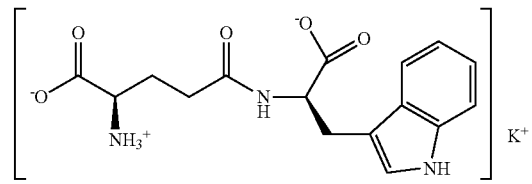

Potassium salt of Formula I

As used herein, the magnesium or calcium salt is formed by the replacement of one carboxylic group hydrogen with the metal ion magnesium or calcium with the structure shown in formula II above. The term "D-isoglutamyl-D-tryptophan calcium salt (2:1)" refers herein to Ca(D-isoglutamyl-D-tryptophan)$_2$. Similarly, the term "D-isoglutamyl-D-tryptophan magnesium salt (2:1)" refers herein to Mg(D-isoglutamyl-D-tryptophan)$_2$. The specific structures are shown below:

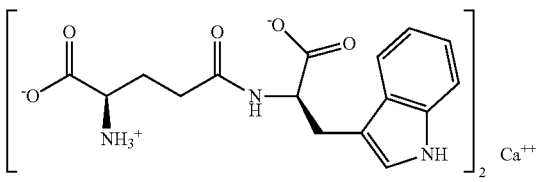

Calcium salt of Formula II

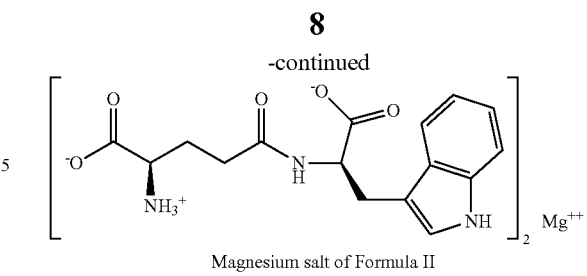

Magnesium salt of Formula II

As used herein, the organic amine salts refer to salts from the peptide and an organic amine. For example, tert-butylamine, N-methyl-D-glucamine and tromethamine are organic amines. The organic amine salt of the present invention is formed by the replacement of one carboxylic group hydrogen with an organic amine with the structure shown in formula III above. For example, the organic amine salt formed from tert-butylamine and D-isoglutamyl-D-tryptophan is referred to herein as D-isoglutamyl-D-tryptophan tert-butylammonium salt (1:1). The specific structure is shown below:

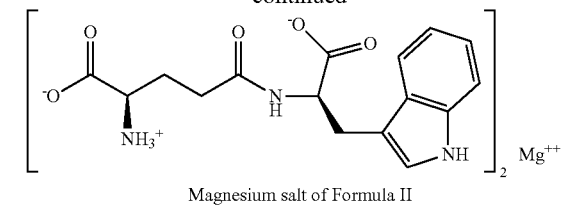

The organic amine salt of the present invention formed from N-methyl-D-glucamine and D-isoglutamyl-D-tryptophan is referred to herein as the D-isoglutamyl-D-tryptophan methyl-(2,3,4,5,6-pentahydroxy-hexyl)-ammonium salt (1:1). The specific structure is shown below:

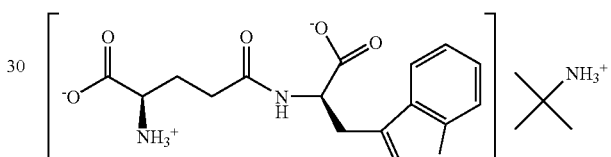

The organic amine salt of the present invention formed from tromethamine and D-isoglutamyl-D-tryptophan is referred to herein as the D-isoglutamyl-D-tryptophan tris(hydroxymethyl)methylammonium salt (1:1). The specific structure is shown below:

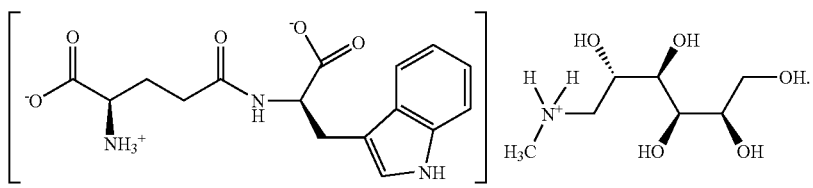

A pharmaceutically acceptable salt of a drug substance is one that is chemically stable and can be used in a pharmaceutical composition. Unlike simple aromatic hydrocarbons, thymodepressin is a dipeptide with multi-functional groups. The dipeptide D-isoglutamyl-D-tryptophan has an alpha amine, two carboxylic acids and an indole nitrogen within the same molecule. An ideal salt should be one that has a solution pH close to about 7 and in the low basic pH range. Through investigations in our laboratory, in the search for a novel salt to address the shortcomings of the disodium salt of D-isoglutamyl-D-tryptophan, the speciation plot (FIG. 5) was used to determine salts with ideal solution pH and solubility that are suitable for pharmaceutical formulations. FIG. 5 is a speciation plot of H-D-iGlu-D-Trp-OH from pH 0 to 12 using experimentally determined pKas. In FIG. 5, $LH_2$=H-D-iGlu-D-Trp-OH, LH=mono carboxylic acid salt, L=dicarboxylic acid salt, and $LH_3$=acid addition salt of H-D-iGlu-D-Trp-OH. The X axis provides the pH of the solution, whereas the Y axis reports the amount of the species present at a particular pH. From our practical experience, we use 6 ml of water per gm of H-D-iGlu-D-Trp-OH for isolation purposes, which corresponds to a concentration of 0.5 M solution.

According to the speciation plot calculation shown in FIG. 5, the diacid form has a pH of about 2.7 to about 3 in solution. The metal salt of formula I wherein M is potassium or lithium; the divalent salt of formula II wherein B is calcium or magnesium has a solution pH close to about 7.

Other salts such as salts of formula IV

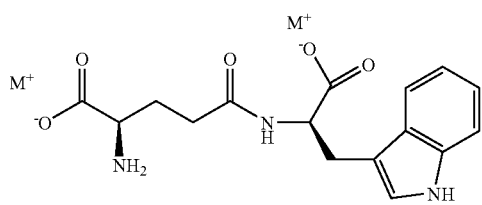

IV wherein M is as defined above, salts of formula V

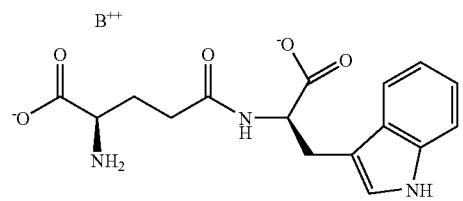

V wherein B is as defined above, and salts of formula VI

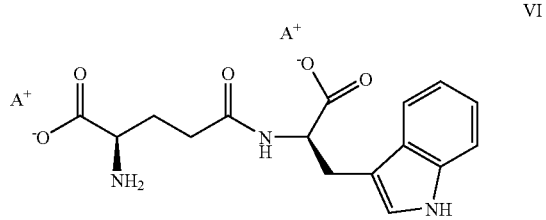

VI wherein A is as defined above, are new salts.

The disodium salt (formula IV wherein M=Na) is a less stable chemical entity as a solid. It is extremely hygroscopic and very difficult to weigh for formulation research. In solution, as per the speciation plot (FIG. 5), the pH is above 9.0 and the solution pH must be adjusted to about 7.0 to about 7.4 in a formulation preparation.

As mentioned above, it has been determined through investigations in our laboratory that the potassium salt of formula I can exist in amorphous or non-crystalline form and in crystalline form, depending on the conditions under which it is obtained, as described in more detail below. The present invention relates to the mono potassium salt of thymodepressin in any of its forms.

In an embodiment of the present invention, the potassium salt of formula I is provided in amorphous form.

In another embodiment of the present invention, the potassium salt of formula I is provided in crystalline form.

In another embodiment of the present invention, the crystalline potassium salt of formula I exhibits an X-ray powder diffractogram, obtained at λ=1.542 Å and using a radiation source of Cu Kα, comprising peaks at an angle 2θ of 9.91, 14.84, 15.81, 18.97, 19.76, 24.04, 24.36, 24.82, 25.48, 27.49, 27.94, 28.42, 30.82, 31.28, 31.69, 32.17, 34.35, 35.81, and 36.96°.

In another embodiment of the present invention, the crystalline potassium salt of formula I has an X-ray powder diffractogram substantially in accordance with that shown in FIG. 1A.

As mentioned above, it has been determined through investigations in our laboratory that the lithium salt of formula I can exist in amorphous or non-crystalline form and in crystalline form, depending on the conditions under which it is obtained, as described in more detail below. The present invention relates to the mono lithium salt of thymodepressin in any of its forms.

In an embodiment of the present invention, the lithium salt of formula I is provided in amorphous form.

In another embodiment of the present invention, the lithium salt of formula I is provided in crystalline form.

In another embodiment of the present invention, the crystalline lithium salt of formula I exhibits an X-ray powder diffractogram, obtained at λ=1.542 Å and using a radiation source of Cu Kα, comprising peaks at an angle at 2θ of 13.57, 15.53, 18.71, 20.11, 23.34, 24.1, 25.09, 27.31, 27.72, 28.39, 29.31, 30.19, 31.21, 32.06, 33.05, 33.62, and 37.41°.

In another embodiment of the present invention, the crystalline lithium salt of formula I has an X-ray powder diffractogram substantially in accordance with that shown in FIG. 2A.

As mentioned above, it has been determined through investigations in our laboratory that the magnesium salt of formula II exists in crystalline form.

In another embodiment of the present invention, the magnesium salt of formula II is provided in crystalline form.

In another embodiment of the present invention, the crystalline magnesium salt of formula II exhibits an X-ray powder diffractogram, obtained at λ=1.542 Å and using a radiation source of Cu Kα, comprising peaks at an angle at 2θ of 12.2, 13.74, 14.84, 16.16, 17.96, 18.52, 18.94, 19.49, 21.05, 21.56, 22.56, 23.36, 24.12, 26.27, 27.65, 28.42, 29.14, 30.55, 31.77, 32.62, 33.26, 35.05, 36.34, 37.22, and 38.05°.

In another embodiment of the present invention, the crystalline magnesium salt of formula II has an X-ray powder diffractogram substantially in accordance with that shown in FIG. 3A.

The percent crystallinity of calcium thymodepressin or the calcium salt of formula II according to the present invention is under about 67%, more preferably under about 50%, and most preferably under about 25%.

In another embodiment of the present invention, the calcium salt of formula II is provided with a degree of crystallinity under about 67%.

The overall crystallinity measured by means of the powder X-ray diffraction technique provides additional helpful information for pharmaceutical materials that contain some amorphous material formed during synthetic procedure. It is also a valuable measure for control of long-term changes in the crystalline materials. Although not related to any structural and compositional features, the measured "percent crystallinity" may be a good indicator of the stability of a particular material as a function of time. The method for determining percent crystallinity of the compound of the present invention is described in the example below. Representative XRPD patterns of the calcium salt of D-isoglutamyl-D-tryptophan are shown in FIGS. 4A and 4B.

In another embodiment of the present invention, there is provided the tert-butylammonium salt of formula III as shown below:

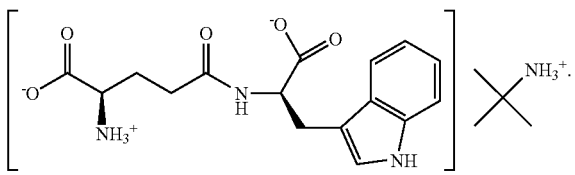

In another embodiment of the present invention, there is provided the tris(hydroxymethyl)methylammonium salt of formula III as shown below:

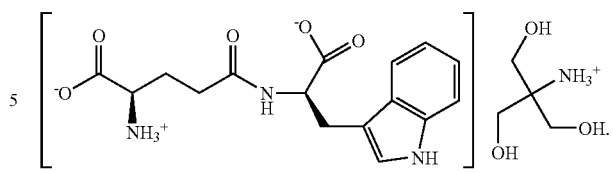

In another embodiment of the present invention, there is provided the methyl-(2,3,4,5,6-pentahydroxy-hexyl)-ammonium salt of formula III as shown below:

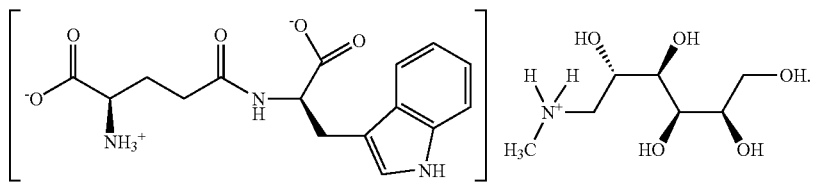

In another embodiment of the present invention, there is provided a process for preparing the lithium or potassium salt of formula I, comprising: (a) reacting D-isoglutamyl-D-tryptophan in water with lithium or potassium hydroxide; (b) concentrating the solution to an oil and adding isopropanol with stirring to cause the precipitation of the salt; recovering the precipitate thereof; and vacuum drying the product to obtain the metal salt of formula I wherein M is lithium, or potassium.

Particularly, the metal carboxylate salt of formula I is formed from reacting a mixture of H-D-iGlu-D-Trp-OH with slightly less than about one equivalent of a metal hydroxide such as potassium hydroxide or lithium hydroxide, and adjusting the pH with the same metal hydroxide to a pH of about 7.0. Solvent evaporation gave an oil, which is treated with isopropanol to precipitate the solid salt. The salt is isolated by conventional means and dried under vacuum to give the product of formula I.

In another embodiment of the present invention, there is provided a process for preparing the calcium salt of formula II, comprising: (a) reacting D-isoglutamyl-D-tryptophan in water with calcium hydroxide; (b) concentrating the solution with stirring to cause the precipitation of the salt; recovering the precipitate thereof; and vacuum drying the product to obtain the metal salt of formula II wherein B is calcium.

Particularly, the calcium salt is prepared by mixing the dipeptide H-D-iGlu-D-Trp-OH with calcium hydroxide, preferably about 0.48-0.49 equivalent of calcium hydroxide per equivalent of H-D-iGlu-D-Trp-OH at ice bath temperature with stirring for several hours, preferably from about 2.5 to about 4 hrs to give a solution. The preferred amount of water is about 12.5 ml of water per gm of H-D-iGlu-D-Trp-OH. The pH of the solution is adjusted with saturated Ca(OH)$_2$ to a pH of about 6 and the insoluble particulates are filtered. The filtrate is evaporated to about 14 to about 16% of its original volume. Upon stirring for about 14 to about 18 hrs at room temperature, a solid is formed and filtered. The calcium salt is dried under vacuum.

In another embodiment of the present invention, there is provided a process for preparing the magnesium salt of formula II, comprising: (a) reacting D-isoglutamyl-D-tryptophan with magnesium ethoxide in isopropanol; (b) concentrating the solution to give a solid; mixing the solution with water; filtering of insoluble particulates; diluting the filtrate with water with stirring to precipitate the product; recovering the precipitate thereof; and vacuum drying the salt of formula II wherein B is magnesium.

Particularly, the magnesium salt is prepared by adding H-D-iGlu-D-Trp-OH to a mixture of magnesium ethoxide in isopropanol at ice bath temperature, preferably about 0.48-0.49 equivalent of magnesium ethoxide is used per equivalent of H-D-iGlu-D-Trp-OH. The mixture is stirred for about 3 to about 10 hrs, preferably about 4 to about 5 hrs. The pH of the solution is tested by withdrawing a sample and mixing it with a few drops of water. Additional magnesium ethoxide is added, preferably from about 0.1 to about 0.12 equivalent of magnesium ethoxide and the mixture is stirred for about 10 to about 18 hrs, preferably for about 14 to about 16 hrs. The pH of the solution is tested by withdrawing a sample and mixing it with a few drops of water and the pH is at about 7.0. The solution is evaporated under reduced pressure to give a solid, which is dissolved in water. The insoluble particulates are filtered and the filtrate is evaporated to give a solid. The solid is mixed with water to form a suspension, and further stirred for about 3 to about 6 hrs to obtain a precipitate. The magnesium salt is filtered and dried under vacuum.

In another embodiment of the present invention, there is provided a process for preparing the organic amine salt of formula II, comprising: (a) reacting D-isoglutamyl-D-tryptophan in water with an organic amine in water wherein the organic amine is tert-butylamine or N-methylglucamine or tromethamine; and (b) concentrating the solution by co-evaporating with isopropanol; adding of acetone to cause the precipitate of the salt; recovering the precipitate thereof; and vacuum drying the product to obtain the organic ammonium salt of formula III wherein A is tert-butylammonium or tris(hydroxymethyl)methylammonium or methyl-(2,3,4,5,6-pentahydroxy-hexyl)-ammonium.

Particularly, the compound of formula III wherein the counterion is an organic amine is prepared by mixing the organic amine with H-D-iGlu-D-Trp-OH in water at ambient temperature and stirring the mixture for about 12 to about 18 hrs. The solvent is co-evaporated with isopropanol and reduced under vacuum to give a solid, which is stirred with acetone and filtered. Examples of organic amines are selected from the group consisting of tris(hydroxymethyl)aminomethane, N-methyl-glucamine and tert-butylamine.

In another embodiment of the present invention, there is provided a method of salt exchange for a D-isoglutamyl-D-tryptophan salt comprising: (a) reacting an ammonium salt represented by the formula VII,

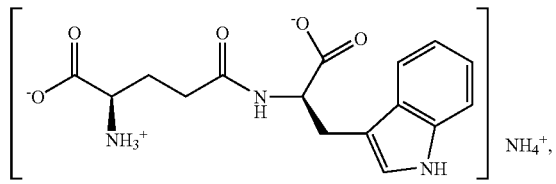

VII in aqueous solution with about one equivalent of a metal hydroxide represented by MOH wherein M is potassium or lithium; and (b) evaporating the solvent to give a solid which is mixed with water and isopropanol to obtain the compound of formula I wherein M is potassium or lithium.

In another embodiment of the present invention, there is provided a method of salt exchange for a D-isoglutamyl-D-tryptophan salt comprising: (a) reacting an ammonium salt represented by the formula VII in aqueous solution with about 0.5 equivalent of a metal hydroxide $B(OH)_2$ wherein B is calcium or magnesium; (b) evaporation of the solvent to give a solid which is mixed with water and isopropanol to obtain the compound of formula II wherein B is calcium or magnesium.

The compound of formula I can be prepared by salt exchange. The stable ammonium salt of H-D-iGlu-D-Trp-OH is used as the starting material. The following is a representative process for the preparation of a compound of formula I. A solution of the H-D-iGlu-D-Trp-OH, ammonium salt (1:1) is mixed with a metal hydroxide in water and stirred for about 15 min to about 2 hrs, preferably for about 15 min to about 45 min. The solvent is removed by evaporation and the residual liquid is mixed with isopropanol to afford a precipitate. The metal hydroxide is selected from the group consisting of lithium hydroxide, and potassium hydroxide. The X-ray powder diffraction patterns of D-isoglutamyl-D-tryptophan potassium salt (1:1) and D-isoglutamyl-D-tryptophan lithium salt (1:1) show that they are crystalline.

When a solution of the H-D-iGlu-D-Trp-OH, ammonium salt (1:1) is mixed with a metal hydroxide in water and stirred for about 15 min to about 2 hrs, preferably for about 15 min to about 45 min, and then freeze-dried, the material so obtained is amorphous. The amorphous forms of the sodium, potassium, or lithium salts of H-D-iGlu-D-Trp-OH can be prepared by this method.

A compound of formula II can be prepared from the exchange of the ammonium salt with calcium hydroxide or magnesium hydroxide. For example, a suspension of H-D-iGlu-D-Trp-OH and a metal hydroxide in water such as calcium hydroxide or magnesium hydroxide is heated to about 50-65° C. for about 1 to about 4 hrs. The solvent is reduced by evaporation. The residual liquid is mixed with isopropanol to precipitate the H-D-iGlu-D-Trp-OH metal salt (2:1). When the metal is magnesium, the metal salt H-D-iGlu-D-Trp-OH magnesium (2:1) obtained is crystalline, as confirmed by the X-ray powder diffraction pattern. When the metal is calcium, the isolated H-D-iGlu-D-Trp-OH calcium (2:1) is semi-crystalline with a degree of crystallinity of less than about 67%.

$^{14}$N-NMR is a useful technique for the characterization of the mono ammonium salt of thymodepressin. The metal salts of formula I & II prepared by the above method are substantially free of the ammonium salt, as evident by the lack of the signal for $NH_4^+$ on $^{14}$N-NMR.

We have applied the speciation plot (FIG. 5) to compute the pH range of the salt forms of the dipeptide H-D-iGlu-D-Trp-OH. As shown in FIG. 5, the salt of formula I or II or III is the predominant species between a pH of about 6 to about 8 and makes them ideal candidates for formulation use or incorporation into pharmaceutical compositions for dosing. This is particular ideal for liquid formulation, sublingual tablets, nasal drops and sprays.

UTILITY AND ADMINISTRATION OF THE INVENTION

The potassium, lithium, calcium, magnesium, and organic amine salts of D-isoglutamyl-D-tryptophan of the present invention may be formulated into pharmaceutical compositions for administration to subjects in a therapeutically active amount and in a biologically compatible form suitable for in vivo administration, i.e. a form of the peptides to be administered in which any toxic effects are outweighed by the therapeutic effects.

According to the speciation plot as shown in FIG. 5, the dominant species at neutral pH is the mono carboxylate form of thymodepressin, that is, the mono sodium salt of the dipeptide D-isoglutamyl-D-tryptophan, if the counterion is sodium. The disodium salt of D-isoglutamyl-D-tryptophan is extremely hygroscopic and is very difficult to handle for dispensing purposes.

The amorphous or crystalline form of the salts of the present invention are ideal candidates to replace the disodium salt in the preparation of different formulations useful in the treatment of the same conditions and/or diseases that thymodepressin is useful in treating, such as, for example, psoriasis. Administration of the novel crystalline and amorphous salts of the present invention as described herein can be via any of the accepted modes of administration for systemically active therapeutic medicaments. These methods include oral, parenteral and otherwise systemic, aerosol or topical forms.

Depending on the intended mode of administration, the compositions of the present invention may be in the form of solid, semi-solid or liquid dosage forms, such as, for example, tablets, suppositories, pills, capsules, powders, liquids, aerosols, suspensions, or the like, preferably in unit dosage forms suitable for single administration of precise dosages. The compositions of the present invention may include at least one conventional pharmaceutical carrier or excipient and crystalline thymodepressin or its pharmaceutically acceptable mono ammonium salt and, in addition, may include other medicinal agents, pharmaceutical agents, carriers, adjuvants, etc.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc., an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington: The Science and Practice of Pharmacy, 21$^{st}$ Edition, 2006, Part 5, Pharmaceutical Manufacturing, Chapters 37, 39, 41-47 and 50, pp. 702-719, 745-775, 802-938, and 1000-1017 (formerly known as Remington's Pharmaceutical Sciences), David B. Troy (Ed.), Lipincott Williams & Wilkins, Baltimore, Md. The composition or formulation to be administered will, in any event, contain a quantity of the active compound(s) in an amount effective to alleviate the symptoms of the subject being treated.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

For the salts of the present invention, either oral or nasal (bronchial) administration is preferred, depending on the nature of the disorder being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 1%-95% active ingredient, preferably 25-70%.

Oral and nasal administration to the lungs can also be effected by aerosol delivery forms. For aerosol administration, the active ingredient is preferably supplied in finely divided form along with a surfactant and a propellant. Typical percentages of active ingredients are from about 0.01 to about 20% by weight, preferably from about 0.04 to about 1.0%.

Surfactants must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olestearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the name SPANS®) and the polyoxyethylene and polyoxypropylene derivatives of these esters. Mixed esters, such as mixed or natural glycerides may be employed. The preferred surface-active agents are the oleates or sorbitan, e.g., those sold under the names ARLACEL® C (Sorbitan sesquioleate), SPAN® 80 (sorbitan monooleate) and SPAN®) 85 (sorbitan trioleate). The surfactant may constitute from about 0.1 to about 20% by weight of the composition, preferably from about 0.25 to about 5%.

The balance of the composition is ordinarily propellant. Liquefied propellants are typically gases at ambient conditions, and are condensed under pressure. Among suitable liquefied propellants are the lower alkanes containing up to five carbons, such as butane and propane; and preferably fluorinated or fluorochlorinated alkanes, such as are sold under the name FREON®. Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

For topical administration, these compositions comprise an effective amount of a compound of this class in admixture with a pharmaceutically acceptable non-toxic carrier. A suitable range of composition would be from about 0.1% to about 10% active ingredient, and the balance carrier, preferably from about 1 to about 2% active ingredient. The concentration of active ingredient in pharmaceutical compositions suitable for topical application will vary depending upon the particular activity of the compound used in conjunction with the condition and subject to be treated. Suitable carriers or medicament vehicles for topical application of these compounds include creams, ointments, lotions, emulsions, solutions and the like.

For example, a suitable ointment for topical application of compounds of the invention contains from about 15 to about 45 percent of a saturated fatty alcohol having 16 to 24 carbon atoms such as cetyl alcohol, stearyl alcohol, behenyl alcohol, and the like and from about 45 to about 85 wt. percent of a glycol solvent such as propylene glycol, polyethylene glycol, dipropylene glycol, and mixtures thereof. The ointment may also contain from about 0 to about 15 wt. percent of a plasticizer such as polyethylene glycol, 1,2,6-hexanetriol, sorbitol, glycerol, and the like; from about 0 to about 15 wt. percent of a coupling agent such as a saturated fatty acid having from 16 to 24 carbon atoms, e.g., stearic acid, palmitic acid, behenic acid, a fatty acid amide e.g., oleamide, palmitamide, stearamide, behenamide and an ester of a fatty acid having from 16 to 24 carbon atoms such as sorbitol monostearate, polyethylene glycol monostearate, polypropylene glycol or the corresponding mono-ester of other fatty acids such as oleic acid and palmitic acid; and from about 0 to about 20 wt. percent of a penetrant such as dimethyl sulfoxide or dimethylacetamide.

A therapeutically active amount of the salts of the present invention may vary according to factors such as disease state, age, sex, and weight of the individual. The dosage regime may be altered to provide the optimum therapeutic response. Generally, the daily regimen should be in the range of from about 1 to about 200 mg of peptide.

The following are examples of representative formulations and in no way restrict the scope of the pharmaceutical compositions encompassed by the present invention.

| Ingredients | Quantity per tablet mgs |
| --- | --- |
| Active ingredient | 25 |
| lactose, spray-dried | 20 |
| Corn starch | 153 |
| magnesium stearate | 2 |

The above ingredients are thoroughly mixed and pressed into single scored tablets.

| Ingredients | Quantity per tablet mgs |
| --- | --- |
| Active ingredient | 100 |
| lactose, spray-dried | 148 |
| magnesium stearate | 2 |

The above ingredients are mixed and introduced into a hard-shell gelatin capsule.

| Ingredients | Quantity per tablet mgs |
| --- | --- |
| Active ingredient | 200 |
| lactose | 145 |
| cornstarch | 50 |
| magnesium stearate | 5 |

The above ingredients are mixed intimately and pressed into single scored tablets.

| Ingredients | Quantity per tablet mgs |
| --- | --- |
| Active ingredient | 108 |
| lactose | 15 |
| cornstarch | 25 |
| magnesium stearate | 2 |

The above ingredients are mixed and introduced into a hard-shell gelatin capsule.

| Ingredients | Quantity per tablet mgs |
| --- | --- |
| Active ingredient | 150 |
| Lactose | 92 |

The above ingredients are mixed and introduced into a hard-shell gelatin capsule.

An injectable preparation buffered to a pH of 7 is prepared having the following composition:

| Ingredients | |
| --- | --- |
| Active ingredient | 0.2 g |
| $KH_2PO_4$ | 2 ml |
| KOH (1N) | q.s. to pH 7 |
| Water (distilled, sterile) | q.s. to 20 ml |

An injectable preparation buffered to a pH of 7 is prepared having the following composition:

| Ingredients | |
| --- | --- |
| Active ingredient | 0.01 g |
| Water (distilled, sterile) | q.s. to 1 ml |
| NaOH (0.2N) | q.s. to pH 7 |

An oral suspension is prepared having the following composition:

| Ingredients | |
| --- | --- |
| Active ingredient | 0.1 g |
| fumaric acid | 0.5 g |
| methyl paraben | 2.0 g |
| granulated sugar | 0.1 g |
| sorbitol (70% solution) | 25.5 g |
| Veegum K (Vanderbilt Co.) | 12.85 g |
| flavoring | 1.0 g |
| colorings | 0.035 ml |
| distilled water | q.s. to 100 ml |

Topical Formulation

| Ingredients | Grams |
| --- | --- |
| Active compound | 0.2-2 |
| Span 60 | 2 |

-continued

| Ingredients | Grams |
|---|---|
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| distilled water | q.s. 100 ml |

All of the above ingredients, except water, are combined and heated to about 45 degrees C. with stirring. A sufficient quantity of water at about 45 degrees C. is then added with vigorous stirring to emulsify the ingredients, and water then added q.s. 100 g.

In the following, the present invention is explained in detail referring to Examples, but the present invention is not limited thereto by any means.

The present invention provides a pharmaceutical composition which comprises the lithium or potassium salt of formula I in any of its forms and one or more pharmaceutically acceptable excipients.

The present invention also provides a pharmaceutical composition which comprises the calcium or magnesium salt of formula II in any of its forms and one or more pharmaceutically acceptable excipients.

The present invention further provides a pharmaceutical composition which comprises an organic amine salt of formula III in any of its forms and one or more pharmaceutically acceptable excipients.

Further details of the preferred embodiments of the present invention are illustrated in the following examples which are understood to be non-limiting with respect to the appended claims.

EXAMPLES

Example 1

Preparation of potassium salt of D-isoglutamyl-D-tryptophan (1:1) from D-isoglutamyl-D-tryptophan and potassium hydroxide.

In a 100-mL round bottom flask equipped with a magnetic stir bar was placed 5 mL of potassium hydroxide solution (0.5 N). The solution was cooled to 0° C. in an ice-water bath, and solid H-D-iGlu-D-Trp-OH (1.00 g, 3 mmol) was added. The mixture was stirred while the pH of the solution was adjusted to ca. 6.0 by adding a few drops of potassium hydroxide solution (0.5 N). The solution was filtered to remove any solid particulates. The filtrate was evaporated to dryness at a bath temperature of about 30° C. to afford a solid. After drying under vacuum at room temperature for overnight, the salt was obtained in quantitative yield, with a HPLC purity (peak area percent) of 98.3%. HPLC method: Column: XTerra MS C18; 5 μm, 4.6×250 mm; Mobile phase: A=the aqueous phase: 4 mM Tris, 2 mM EDTA, pH 7.4; B=the organic phase: $CH_3CN$; gradient: B %: 0 min. 5%, 15 min. 55%, 30 min. 55%, 32 min. 5%, 35 min. 5%; Flow rate: 1 mL/min; injection volume: 5 μL; λ: 222, 254, 282, 450 nm; retention time of the product: 6.41 min. The XRPD pattern of this crystalline material is shown in FIG. 1A; the water content by Karl-Fischer test is 0.7%; UV (water, c=23.8 μM, $\lambda_{max}$ nm): 221 (ε33270), 280 (ε5417); MS (m/z): 372.0 [M]$^+$, 334.2 [$C_{16}H_{20}N_3O_5$]$^+$, 187.9 (100%). The FT-IR (KBr) spectrum is shown in FIG. 1B.

Example 2

A. Preparation of mono potassium salt of D-isoglutamyl-D-tryptophan (1:1) from the mono ammonium salt of D-isoglutamyl-D-tryptophan (1:1).

A solution of H-D-iGlu-D-Trp-OH, mono ammonium salt (1:1), (1.66 g, 4.05 mmol) and potassium hydroxide (253 mg, 4.50 mmol) in water (20 mL) was stirred at room temperature for 15 min. The pH of the solution was about 9. The reaction mixture was evaporated under reduced pressure to a volume of about 1 mL. After cooling to room temperature, isopropanol was added until a solid precipitated out. The resulting suspension was stirred at room temperature for 15 min, then filtered. The solid was washed with isopropanol (2×20 mL) and ethyl acetate (20 mL), then dried under vacuum in an oven at 42° C. overnight. An off white solid was obtained (1.49 g, 99% yield). The water content by Karl-Fischer test is 2.5%. Analytical data (XRPD pattern, FT-IR and MS spectra) are similar to those described in Example 1.

B. Preparation of amorphous form of potassium salt of D-isoglutamyl-D-tryptophan (1:1) from the mono ammonium salt of D-isoglutamyl-D-tryptophan (1:1).

A solution of H-D-iGlu-D-Trp-OH, mono ammonium salt (1:1), (517 mg, 1.40 mmol) and potassium hydroxide (82 mg, 1.46 mmol) in water (10 mL) was stirred at room temperature for 30 minutes. The resulting mixture was freeze-dried overnight. An off white solid was obtained in quantitative yield. The XRPD pattern spectrum confirmed that this material is amorphous. $^1$H NMR ($D_2O$) δ: 7.69 (d, J=7.9 Hz, 1H), 7.48 (d, J=8.2 Hz, 1H), 7.23 (t, J=7.6 Hz, 1H), 7.22 (s, 1H), 7.16 (t, J=7.4 Hz, 1H), 4.59 (dd, J=8.7, 4.8 Hz, 1H), 3.51 (dd, J=6.8, 5.8 Hz, 1H), 3.38 (dd, J=14.8, 4.8 Hz, 1H), 3.11 (dd, J=14.8, 8.8 Hz, 1H), 2.20-2.49 (m, 2H) and 1.85-1.94 (m, 2H); $^{13}$C NMR ($D_2O$) δ: 181.4, 177.0, 176.6, 138.8, 129.9, 126.9, 124.5, 121.9, 121.4, 114.5, 113.2, 58.6, 57.0, 34.6 ($CH_2$), 30.2 ($CH_2$) and 29.3 ($CH_2$); the water content by Karl-Fischer test is 5.4%; the FT-IR (KBr) spectrum is shown in FIG. 1C; MS (m/z): 371.7 [M]$^+$, 334.2 [$C_{16}H_{20}N_3O_5$]$^+$, 187.9 (100%); HPLC purity (peak area percent): 99.8%, Retention time: 5.04 min; HPLC conditions: Column Waters Symmetry C18, 3.9×150 mm, 5 μm; Mobile phase: 0.035% $HClO_4$, pH 2/$CH_3CN$, 85/15, isocratic, Flow rate: 1 mL/min; λ: 220, 254, 280 nm.

Example 3

A. Preparation of lithium salt of D-isoglutamyl-D-tryptophan (1:1) from mono ammonium salt of D-isoglutamyl-D-tryptophan (1:1) and lithium hydroxide monohydrate.

A solution of H-D-iGlu-D-Trp-OH, mono ammonium salt (1:1), (1.40 g, 3.80 mmol) and lithium hydroxide monohydrate (159 mg, 3.80 mmol) in water (20 mL) was stirred at room temperature for 20 min. The pH of the solution was about 9. The reaction mixture was evaporated under reduced pressure to about 2 mL of solvent. After cooling down to room temperature, isopropanol was added until a solid precipitated out. The resulting suspension was stirred at room temperature for 20 min, then filtered. The solid was washed with isopropanol (2×20 mL) and ethyl acetate (20 mL), then dried under vacuum in an oven at 42° C. for overnight. The product was obtained as an off white solid in quantitative yield. The XRPD pattern of this crystalline material is shown in FIG. 2A. The water content by Karl-Fischer test is 10.7%. MS (m/z): 340.1 [M+1]$^+$, 334.3 [$C_{16}H_{20}N_3O_5$]$^+$, 187.9 (100%). The FTIR (KBr) spectrum is shown in FIG. 2B.

B. A solution of H-D-iGlu-D-Trp-OH, mono ammonium salt (1:1), (480 mg, 1.30 mmol) and lithium hydroxide monohydrate (57 mg, 1.36 mmol) in water (10 mL) was stirred at room temperature for 30 min. The resulting mixture was freeze dried overnight. The product was obtained as an off white solid in quantitative yield. The XRPD pattern confirmed that this material is amorphous. $^1$H NMR (D$_2$O) δ: 7.69 (d, J=7.8 Hz, 1H), 7.50 (d, J=8.2 Hz, 1H), 7.23 (t, J=7.1 Hz, 1H), 7.22 (s, 1H), 7.16 (t, J=7.5 Hz, 1H), 4.57 (dd, J=8.7, 4.8 Hz, 1H), 3.36-3.43 (m, overlapping t and dd, 2H), 3.12 (dd, J=14.7, 8.7 Hz, 1H), 2.20-2.35 (m, 2H) and 1.78-1.92 (m, 2H); $^{13}$C NMR (D$_2$O) δ: 181.4, 178.1, 176.7, 138.8, 129.9, 126.9, 124.5, 121.9, 121.4, 114.5, 113.2, 58.6, 57.1, 34.7 (CH$_2$), 30.2 (CH$_2$) and 29.3 (CH$_2$); the FT-IR (KBr) spectrum is shown in FIG. 2C; The water content by Karl-Fischer test is 11.5%. The MS spectrum is similar to that of Example 3A; HPLC purity (peak area percent): 99.8%, Retention time: 5.10 min. The HPLC conditions described in Example 2B was used.

Example 4

Preparation of lithium salt of D-isoglutamyl-D-tryptophan (1:1) from D-isoglutamyl-D-tryptophan and lithium hydroxide monohydrate.

A. In a 100 mL round bottom flask equipped with a magnetic stir bar was dissolved lithium hydroxide monohydrate (125.8 mg, 2.99 mmol) in 10 mL of water. The solution was cooled to 0° C. using an ice bath. H-D-iGlu-D-Trp-OH (1.00 g, 3 mmol) was suspended in the solution. The solid slowly dissolved over 2.5 h, and a clear pale pink solution was obtained. After an additional 30 minutes of stirring, the mixture was warmed to room temperature. The solution was filtered and carefully concentrated to a volume of about 4 mL. Isopropanol (25 mL) was added slowly until solid began to form. The solution was filtered and the solid divided into two equal parts.

B. One part of the solid from section A was washed with isopropanol (2×15 mL). The solid was first air dried and then dried under vacuum in the oven (35° C.) overnight. The water content by Karl-Fischer test is 10.6%. The XRPD pattern and the MS and FT-IR (KBr) spectra of this compound are similar to those described in Example 3A.

C. The second part of the solid was washed with isopropanol (2×15 mL), then with ethyl acetate (2×10 mL). The solid was first air dried and then dried under vacuum in the oven (35° C.) for overnight. The XRPD pattern and the FT-IR (KBr) spectrum of this compound are similar to those described in Example 3A.

The combined material from sections B and C is 0.99 g (97.6% yield).

Example 5

Preparation of magnesium salt of D-isoglutamyl-D-tryptophan (1:2) from D-isoglutamyl-D-tryptophan.

In a 100-mL round bottom flask equipped with a magnetic stir bar was placed magnesium ethoxide (Aldrich, 98%, 0.206 g, 1.76 mmol) and isopropanol (15 mL). The solution was cooled to 0° C. in an ice-water bath, and solid H-D-iGlu-D-Trp-OH (1.20 g, 3.60 mmol) was added. The white suspension was stirred at room temperature for 4 h. 2 to 3 drops of the reaction mixture was placed in a test tube, and a few drops of deionized water was added. The mixture was vortexed to give a clear solution. The pH of the solution was 4.0 to 4.5. To the reaction mixture was added magnesium ethoxide (Aldrich, 98%, 0.050 g, 0.43 mmol). The mixture was stirred at room temperature for overnight. 2-3 drops of the white suspension was placed in a test tube, and a few drops of deionized water were added. The mixture was vortexed to give a clear solution. The pH of the solution was about 7.0. The mixture was evaporated to dryness at a bath temperature of 30° C. to give a white solid. The residue was dissolved in 15 mL of deionized water to give a yellow solution. The latter was filtered to remove any solid particulates. The filtrate was evaporated to dryness at a bath temperature of 30° C. to give a solid. The solid was suspended in deionized water (20 mL), and the mixture was stirred for 3 h. The solid was collected by filtration and washed with ice-cold deionized water (2×6 mL). The solid was air-dried first, and then placed in a vacuum oven at 42° C. for overnight. Thus, 0.88 g (72% yield, HPLC purity (peak area percent): 99.1%) of the product was obtained. The HPLC method described in Example 1 was used. The retention time for this product is 6.39 min. The XRPD pattern spectrum of this crystalline material is shown in FIG. 3A. The water content by Karl-Fischer test is 12.2%. MS (m/z): 689.3 [M]$^+$, 334.2 [C$_{16}$H$_{20}$N$_3$O$_5$]$^+$, 187.9 (100%). UV (water, c=11.7 μM, λ$_{max}$ nm): 221 (ε57906), 280 (ε9449). The FT-IR (KBr) spectrum is shown in FIG. 3B.

Example 6

Preparation of magnesium salt of D-isoglutamyl-D-tryptophan (1:2) from the mono ammonium salt of D-isoglutamyl-D-tryptophan (1:1).

A suspension of D-isoglutamyl-D-tryptophan, mono ammonium salt (1:1), (1.53 g, 4.15 mmol) and magnesium hydroxide in H$_2$O (20 mL) was heated between 55° C. to 60° C. for 3 h. The resulting yellowish suspension was evaporated under reduced pressure to about 1-2 mL. Then isopropanol (30 mL) was added. The suspension was stirred for 20 min at room temperature, then filtered. The solid was washed successively with isopropanol (2×20 mL) and ethyl acetate (20 mL), then dried in a vacuum oven at 42° C. for overnight. A yellowish solid was obtained (1.5 g). The water content by Karl-Fischer test is 8.8%. Analytical data (XRPD pattern and FT-IR and MS spectra) are similar to those described in Example 5.

Example 7

Preparation of the calcium salt of D-isoglutamyl-D-tryptophan (1:2) from D-isoglutamyl-D-tryptophan (1:1) and calcium hydroxide.

In a 100-mL round bottom flask equipped with a magnetic stir bar was placed calcium hydroxide (Aldrich, 99.99%, less than 3% calcium carbonate, 0.2603 g, 3.51 mmol) and deionized water (30 mL). The cloudy solution was cooled to 0° C. in an ice-water bath, and solid H-D-iGlu-D-Trp-OH (2.404 g, 7.2 mmol) was added. The mixture was stirred for 2.5 h to give a clear slightly pinkish solution. The pH of the solution was adjusted to 6.0 by adding saturated calcium hydroxide solution. The solution was filtered to remove any solid particulates. The filtrate was divided into two equal volume (about 20 mL each): solution A and solution B.

Solution A was reduced by rotary evaporation to about 4-5 mL using a water bath set to about 30° C. It was still a clear solution. This concentrated solution was stirred vigorously at room temperature for 17 h to give a solid. The solid was filtered by filtration and washed with ice-cold deionized water (3×6 mL). The solid was air-dried first, and then dried in a vacuum oven at 40° C. overnight to give a solid 0.70 g (55%, HPLC purity by area %: 97.7). The HPLC method described in Example 1 was used. The retention time for this product is 6.39 min. The XRPD pattern of this material is shown in FIG. 4A.

The water content by Karl-Fischer test is 5.4%. MS (m/z): 705.6 [M+1]$^+$, 334.2 [C$_{16}$H$_{20}$N$_3$O$_5$]$^+$, 187.9 (100%). UV (water, c=10.8 μM, $\lambda_{max}$ nm): 221 (ε61014), 280 (ε9943). The FT-IR (KBr) spectrum is shown in FIG. 4C.

Solution B was evaporated to dryness. Deionized water (6 mL) was added and the mixture was stirred for 16 h. The insoluble solid was filtered and dried under high vacuum at 35° C. for 48 h (0.53 g). The XRPD pattern is similar to that reported in FIG. 4A.

Example 8

Preparation of the calcium salt of D-isoglutamyl-D-tryptophan (1:2) from mono ammonium salt of D-isoglutamyl-D-tryptophan (1:1) and calcium hydroxide.

A suspension of mono ammonium salt (1:1) of D-isoglutamyl-D-tryptophan, (1.49 g, 4.06 mmol) and calcium hydroxide (150 mg, 2.03 mmol) in water (20 mL) was heated between 55° C. to 60° C. for 1 h. The resulting solution was evaporated under reduced pressure to about 1-2 mL. Isopropanol (30 mL) was added. The suspension was stirred for 20 min at room temperature, then filtered. The solid was washed successively with isopropanol (2×20 mL) and ethyl acetate (20 mL), then dried in oven at 42° C. overnight. An off white solid was obtained (1.45 g). The XRPD pattern of this semi-crystalline material is shown in FIG. 4B. This material has a lower degree of crystallinity than that isolated in Example 7. The water content by Karl-Fischer test is 6.2%. MS (m/z): 705.4 [M+1]$^+$, 334.2 [C$_{16}$H$_{20}$N$_3$O$_5$]$^+$, 187.9 (100%).

Example 9

Percent Crystallinity of calcium salt of D-iGlu-D-Trp by means of x-ray powder diffraction method.

The overall crystallinity measured by means of the XRPD technique provides additional helpful information for pharmaceutical materials that contain some amorphous material formed during synthetic procedure. It is also a valuable measure for control of long-term changes in the crystalline materials. Although not related to any structural and compositional features, the measured "percent crystallinity" may be a good indicator for the stability of a particular material as a function of time.

The percent crystallinity is commonly measured as a ratio between the diffraction portion from the crystalline part of the sample, $I_C$, and the total diffraction from the same sample, $I_{C+B}$. The values of $I_C$ can be obtained after an appropriate subtraction of the scattering portion from the background, $I_B$.

For such kind of analyses, the diffraction is measured as total area under the profile of:
- the whole pattern as it is collected (one may correct for the air scattering)—$I_{TOTAL}$.
- the peaks only ($I_C$) after subtraction of the background (correction for the air scattering),
- the background only with correction for air scattering—($I_B$)

$$C, \% = \frac{I_c}{I_{total}} \cdot 100, \text{ where: } I_{total} = I_c + I_b.$$

It is worthy to note that this measurement is not recommended to be standardized—it is very difficult (almost impossible) for inter-laboratory results to be compared. Every diffractometer has its own scale of displaying the background level and the peak heights and areas depending on many instrumental and sample preparation factors.

The above approach is possible mostly for "point-detector" diffractometers in which the detector is moving with synchronised twice greater speed than the sample in order to ensure the theta/2theta constant ratio.

However, in this study, due to the technical problems with the D5000 point-detector diffraction system, all the samples were analyzed on a D8 system, equipped with an area, 2D detector, and the above-mentioned approach could not be applied. Therefore, another technique has been developed for measuring the crystallinity of samples analyzed on such system. Only a narrow part of the 2D diffraction image is chosen with a single peak at the centre and a neighbour area where the background will be measured.

Samples prepared in Example 8 have % crystallinity of around 18-20%, while samples prepared by the method of Example 7 have a % crystallinity range between 25 to 50%.

The percent crystallinity of a sample can be improved by taking a sample and dissolving it in water. The insoluble particulate is filtered and the solid is allowed to slowly precipitate out of solution.

All samples were measured for calculation of their crystallinity using a narrow range of 21°-25° with a strongest reflection at 13°. The background was subtracted as linear, and an empirical correlation coefficient of 2.5 was applied.

As was pointed out above, the results thus obtained for crystallinity of the semi-crystalline samples should not be considered as absolute ones. None of samples from this structural type possess crystalline order high enough to be considered as absolute reference standard. Examples 7 and 8 produce calcium salt of thymodepressin (1:2) with various percent crystallinity.

Example 10

Preparation of mono tert-butylamine salt of D-isoglutamyl-D-tryptophan (1:1) from D-isoglutamyl-D-tryptophan and tert-butylamine.

A. To a suspension of D-iGlu-D-Trp (1.00 g, 3.00 mmol) in 25 mL of deionized water was added 0.7 mL (2.22 equiv) of tert-butylamine at room temperature (RT). The reaction mixture was clear and the pH of the solution was about 9. After stirring at RT for 1 h, isopropanol was added, and volatile materials were removed in vacuo. The residual solid was suspended in acetone, and the solid was collected by suction filtration. The solid was dried under vacuum at 40° C. for overnight to afford 1.16 g (95% yield) of the mono amine salt. $^1$H NMR confirmed that the product is a mono addition salt. The XRPD pattern confirmed that this material is amorphous. $^1$H NMR (D$_2$O) δ: 7.71 (d, J=8.6 Hz, 1H), 7.39 (d, J=8.1 Hz, 1H), 7.13-7.16 (m, 2H), 7.07 (t, J=7.6 Hz, 1H), 4.48 (dd, J=8.3, 4.9 Hz, 1H), 3.44 (t, J=6.4 Hz, 1H), 3.28 (dd, J=14.8, 4.7 Hz, 1H), 3.02 (dd, J=14.7, 8.7 Hz, 1H), 2.18-2.26 (m, 2H), 1.76-1.97 (m, 2H) and 1.26 (s, 9H). $^{14}$N NMR (D$_2$O) δ (ppm): 40.2 (br) and 56.3 (s), *NH$_4$NO$_3$ was used as external reference with the reference signal set at 20.689 ppm. The water content by Karl-Fischer test is 4.0%. MS (m/z): 407.3 [M+1]$^+$ (weak), 334.2 [C$_{16}$H$_{20}$N$_3$O$_5$]$^+$, 187.9 (100%). The IR spectrum is shown in FIG. 6. UV (water, c=34.8 μM, $\lambda_{max}$ nm): 220 (ε31067), 280 (ε5112).

B. To a suspension of D-iGlu-D-Trp (1.00 g, 3.00 mmol) in 25 mL of deionized water was added 0.31 mL (1.0 equiv) of tert-butylamine at room temperature (RT). The reaction mixture was clear and the pH of the solution was about 9. After stirring at RT for 1 h, isopropanol was added, and volatile materials were removed in vacuo. The residual solid was suspended in acetone, and the solid was collected by suction filtration. The solid was dried under vacuum at 40° C. for overnight to afford 1.16 g (95% yield) of the amine salt. The analytical data obtained for this compound (XRPD, ¹H NMR, MS, FT-IR) are similar to those described in Example 10A above.

Example 11

Preparation of mono tris(hydroxymethyl)aminomethane salt of D-isoglutamyl-D-tryptophan (1:1) from D-isoglutamyl-D-tryptophan and tris(hydroxymethyl)aminomethane (TRIS).

To a suspension of D-iGlu-D-Trp (1.00 g, 3.00 mmol) in 20 mL of deionized water was added a solution of 363 mg (1.0 equiv) of tris(hydroxymethyl)aminomethane (TRIS) in 15 mL of deionized water at RT. The reaction mixture was clear and the pH of the solution was about 7. After stirring at RT for overnight, isopropanol was added, and volatile materials were removed in vacuo. Attempts to recrystallize the compound using a mixture of isopropanol/water or methanol/diethyl ether failed. The residual solid was suspended in acetone and stirred at RT for 1 h, and the solid was collected by suction filtration. The solid was dried under vacuum at 40° C. for overnight to afford 1.33 g of the product (97.5% yield). ¹H NMR (D$_2$O) δ: 7.61 (d, J=7.9 Hz, 1H), 7.41 (d, J=8.1 Hz, 1H), 7.14-7.17 (m, 2H), 7.08 (t, J=7.4 Hz, 1H), 4.48 (dd, J=8.5, 4.8 Hz, 1H), 3.64 (s, 6H), 3.46 (t, J=6.0 Hz, 1H), 3.28 (dd, J=14.8, 4.7 Hz, 1H), 3.02 (dd, J=14.7, 8.7 Hz, 1H), 2.17-2.28 (m, 2H) and 1.74-1.90 (m, 2H). The water content by Karl-Fischer test is 3.3%. MS (m/z): 454.9 [M+1]$^+$ (weak), 334.0 [C$_{16}$H$_{20}$N$_3$O$_5$]$^+$, 187.9 (100%). The IR spectrum is shown in FIG. 7; UV (water, c=36.4 μM, λ$_{max}$ nm): 220 (ε28373), 280 (ε4537).

Example 12

Preparation of mono N-methyl-D-glucamine salt of D-isoglutamyl-D-tryptophan (1:1) from D-isoglutamyl-D-tryptophan and N-methyl-D-glucamine.

To a suspension of D-iGlu-D-Trp (1.00 g, 3 mmol) in 20 mL of deionized water was added a solution of 586 mg (1.0 equiv) of N-methyl-D-glucamine in 15 mL of deionized water at RT. The reaction mixture was stirred for over the weekend at RT. The reaction mixture was clear and the pH of the solution was about 7. Isopropanol was added, and volatile materials were removed in vacuo. The residual solid was suspended in acetone and the solid was collected by suction filtration. The solid was dried under vacuum at 40° C. for overnight to afford the product in quantitative yield. The XRPD pattern confirmed that this material is amorphous. ¹H NMR (D$_2$O) δ: 7.61 (d, J=7.9 Hz, 1H), 7.41 (d, J=8.1 Hz, 1H), 7.15-7.18 (m, 2H), 7.08 (t, J=7.5 Hz, 1H), 4.47 (dd, J=8.6, 4.8 Hz, 1H), 3.99-4.02 (m, 1H), 3.70-3.75 (m, 2H), 3.65-3.68 (m, 1H), 3.54-3.60 (m, 2H), 3.45 (t, J=6.2 Hz, 1H), 3.27 (dd, J=14.8, 4.7 Hz, 1H), 3.02-3.13 (m, 3H), 2.68 (s, 3H), 2.19-2.26 (m, 2H) and 1.75-1.95 (m, 2H). ¹⁴N NMR (D$_2$O) δ (ppm): 29.6 and 39.2 (br. overlapping), *NH$_4$NO$_3$ was used as external reference with the reference signal set at 20.689 ppm. The water content by Karl-Fischer test is 3.1%. MS (m/z): 529.5 [M+1]$^+$, 334.2 [C$_{16}$H$_{20}$N$_3$O$_5$]$^+$, 187.9 (100%). The IR spectrum is shown in FIG. 8. UV (water, c=41.2 μM, λ$_{max}$ nm): 220 (ε27341), 280 (ε4419).

Example 13

Representative procedure for the preparation of D-isoglutamyl-D-tryptophan, mono ammonium salt (1:1) from H-D-iGlu-D-Trp-OH H-D-iGlu-D-Trp-OH (1 g) was mixed with ammonium hydroxide (0.55M, 6 mL). The mixture was stirred and the pH was measured to be around 4.5. Ammonium hydroxide (0.55M) was added dropwise until the pH of the solution reached between 7.0 to 7.5. Volatile materials were removed in vacuo, and the residual oil was mixed with isopropanol. A white precipitate appeared. After 2 h, the solid ammonium salt was collected by suction filtration. The solid was dried to constant weight (1 g) under high vacuum for 12 h to give the D-isoglutamyl-D-tryptophan, ammonium salt (1:1).

Although preferred embodiments of the invention have been described herein, it will be understood by those skilled in the art that variations may be made thereto without departing from the spirit of the invention or the scope of the appended claims.

The invention claimed is:

1. A pharmaceutically acceptable salt of D-isoglutamyl-D-tryptophan of formula I

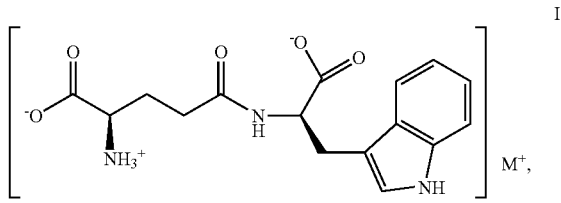

wherein M is potassium, the salt is in crystalline form and is characterized by peaks in an X-ray powder diffraction pattern having the following 2-theta values: 9.91, 14.84, 15.81, 18.97, 19.76, 24.04, 24.36, 24.82, 25.48, 27.49, 27.94, 28.42, 30.82, 31.28, 31.69, 32.17, 34.35, 35.81, and 36.96°.

2. The pharmaceutically acceptable salt of claim 1 characterized by an X-ray powder diffraction pattern as shown in FIG. 1A.

3. A pharmaceutically acceptable salt of D-isoglutamyl-D-tryptophan of formula II

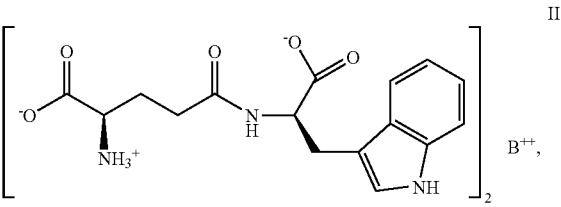

wherein B is magnesium, the salt is in crystalline form and characterized by an X-ray powder diffraction pattern having peaks with 2-theta values of: 12.2, 13.74, 14.84, 16.16, 17.96, 18.52, 18.94, 19.49, 21.05, 21.56, 22.56, 23.36, 24.12, 26.27, 27.65, 28.42, 29.14, 30.55, 31.77, 32.62, 33.26, 35.05, 36.34, 37.22, and 38.05°.

4. The pharmaceutically acceptable salt of claim 3 characterized by an X-ray powder diffraction pattern as shown in FIG. 3A.

5. A pharmaceutical composition comprising a pharmaceutically acceptable salt of claim 1.

6. A pharmaceutical composition comprising a pharmaceutically acceptable salt of claim 2.

7. A pharmaceutical composition comprising a pharmaceutically acceptable salt of claim 3.

8. A pharmaceutical composition comprising a pharmaceutically acceptable salt of claim 4.

* * * * *